United States Patent [19]

Sendai et al.

[11] Patent Number: 4,971,963
[45] Date of Patent: Nov. 20, 1990

[54] CEPHEM COMPOUNDS, AND USE

[75] Inventors: Michiyuki Sendai, Osaka; Shoji Kishimoto, Hyogo, both of Japan

[73] Assignee: Takeda Chemical Industries, Ltd., Osaka, Japan

[21] Appl. No.: 323,915

[22] Filed: Mar. 15, 1989

[30] Foreign Application Priority Data

Mar. 15, 1988 [JP] Japan .................. 63-62815
Nov. 17, 1988 [JP] Japan .................. 63-292185

[51] Int. Cl.$^5$ .................. C07D 501/36; A61K 31/545
[52] U.S. Cl. .................. 514/206; 540/225; 540/227
[58] Field of Search .............. 540/227, 225; 514/206, 514/202

[56] References Cited

U.S. PATENT DOCUMENTS

| | | | |
|---|---|---|---|
| 4,098,888 | 7/1978 | Ochiai et al. | 424/246 |
| 4,264,595 | 4/1981 | Numata et al. | 424/246 |
| 4,331,666 | 5/1982 | Nannini et al. | 424/246 |
| 4,510,138 | 4/1985 | Ochiai et al. | 514/206 |
| 4,681,877 | 7/1987 | Muto et al. | 514/206 |
| 4,788,185 | 11/1988 | Miyake et al. | 514/205 |

FOREIGN PATENT DOCUMENTS 0150507 8/1985 European Pat. Off. .

Primary Examiner—Nicholas S. Rizzo
Attorney, Agent, or Firm—Wegner & Bretschneider

[57] ABSTRACT

An antibacterial agent is provided which is a cephem compound of the formula:

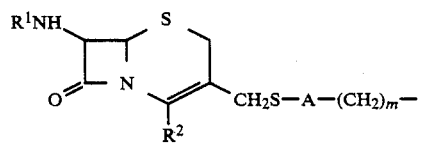

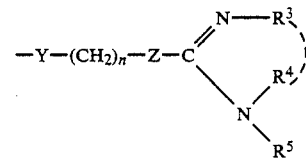

wherein $R^1$ is an acyl group; $R^2$ is a carboxy group which may be esterified; $R^3$ is a hydrogen atom, a lower alkyl group or cyano group; $R^4$ is a hydrogen atom or a lower alkyl group, or $R^4$ together with $R^3$ is a methylene chain having 2 or 3 carbon atoms; $R^5$ is a hydrogen atom or a lower alkyl group; A is an optionally substituted bivalent aromatic heterocyclic group which is bonded to a ring-constituting carbon atom with the adjacent sulfur atom; Y is a binding arm, sulfur or oxygen atom, —NH—, —CONH— or —NHCO—; Z is a binding bond or —NH—; m is an integer of 0 to 4 and n is an integer of 0 to 6, or a pharmacologically acceptable salt thereof.

14 Claims, No Drawings

CEPHEM COMPOUNDS, AND USE

BACKGROUND OF THE INVENTION

1. Field of the Invention

This invention relates to novel cephem compounds possessing excellent antibacterial activities, their production and use. The cephem compounds of the invention are useful as the antibacterial agents.

2. Description of the Prior Art

Various cephalosporin compounds have been prepared as disclosed in e.g., U.S. Pat. Nos. 4,098,888; 4,264,595 and 4,510,138 and U.S. patent application Ser. Nos. 941,169; 943,056 and 943,058. Presently, a variety of cephem compounds have been launched into markets, but there is still the need for creating cephem compounds having potent antibacterial activities against a broad spectrum of Gram -positive bacteria and Gram-negative bacteria as well as possessing other characteristics. The cephem compounds of this invention are novel ones which are not described in printed publications.

SUMMARY OF THE INVENTION

This invention provides a cephem compound of the formula (I):

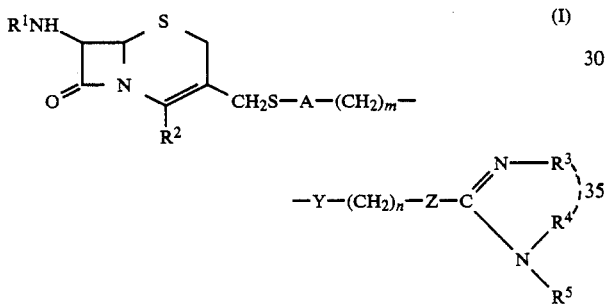

wherein $R^1$ is an acyl group; $R^2$ is a carboxy group which may be esterified; $R^3$ is a hydrogen atom, a lower alkyl group or cyano group; $R^4$ is a hydrogen atom or a lower alkyl group or $R^4$ together with $R^3$ is a methylene chain having 2 or 3 carbon atoms; $R^5$ is a hydrogen atom or a lower alkyl group; A is an optionally substituted bivalent aromatic heterocyclic group which is bonded on a ring-constituting carbon atom with the adjacent sulfur atom; Y is a binding arm, sulfur or oxygen atom, —NH—, —CONH— or —NHCO—; Z is a binding arm or —NH—; m is an integer of 0 to 4 and n is an integer of 0 to 6, or a pharmacologically acceptable salt thereof.

Also, it provides a process for producing the compound (I) or a salt thereof and a pharmaceutical composition comprising the compound (I) or a salt thereof.

The compounds (I) and salts thereof show very potent activities against various Gram-negative bacteria as well as Gram-positive bacteria, e.g., *Staphylococcus aureus*, methicillin-resistant *Staphylococcus aureus* and can exert a long-lasting effect while maintaining a good blood level of the compounds (I) after their administration.

PREFERRED EMBODIMENT OF THE INVENTION

In the above mentioned formula (I), the acyl group of $R^1$ means an acyl group derived from organic carboxylic acids; for example, formyl; an alkylcarbonyl (alkanoyl), preferably, a $C_{1-6}$ alkylcarbonyl (such as acetyl, propionyl, butyryl, isobutyryl, valeryl, isovaleryl, pivaloyl or hexanoyl); an arylcarbonyl (aroyl), preferably a $C_{6-14}$ arylcarbonyl (such as benzoyl or 1- or 2-naphthoyl); an aralkylcarbonyl, preferably a $C_{7-19}$ aralkylcarbonyl (such as benzylcarbonyl, 2-phenethylcarbonyl, 1 or 2-naphthylmethylcarbonyl or benzhydrylcarbonyl); a five- or six-membered aromatic heterocycle-carbonyl (such as 2 or 3-thenoyl, 2 or 3-furoyl, nicotinoyl, isonicotinoyl, 4 or 5-thiazolylcarbonyl, or 1,2,4-thiazol-3 or 5-ylcarbonyl); a five- or six-membered aromatic heterocycle-acetyl (such as 2- or 3-thienylacetyl, 2 or 3-furylacetyl, 4-thiazolylacetyl, 1,2,4-thiadiazol-3-ylacetyl or 1-tetrazoylacetyl); an alkoxycarbonyl, preferably a $C_{1-6}$ alkoxycarbonyl (such as methoxycarbonyl, ethoxycarbonyl, propoxycarbonyl, isopropoxycarbonyl, butoxycarbonyl, isobutoxycarbonyl, tert -butoxycarbonyl); an aryloxycarbonyl, preferably a $C_{6-14}$ aryloxycarbonyl (such as phenoxycarbonyl or 1 or 2-naphthoxycarbonyl); and an aralkyloxycarbonyl, preferably a $C_{7-19}$ aralkyloxycarbonyl (such as benzyloxycarbonyl). These acyl groups may be substituted by amino, nitro, a halogen (such as fluorine, chlorine or bromine), hydroxy, oxo, carbamoyl, a $C_{1-4}$ alkyl (such as methyl, ethyl, propyl, isopropyl or butyl), a $C_{1-4}$ alkoxy (such as methoxy, ethoxy, propoxy or butoxy), a carboxyl which may be esterified, a $C_{1-4}$ alkoxyimino which may be substituted by carboxyl (such as methoxyimino, ethoxyimino, carboxymethoxyimino, 1-carboxy-1-methylethoxyimino), hydroxymino, 4-ethyl-2,3-dioxopiperadinocarbonylamino or the like. The heterocyle in the above mentioned five- or six-membered aromatic heterocycle-carbonyl or five- or six-membered aromatic heterocycle-acetyl includes aromatic heterocycles containing 1 to 4 hetero atoms of nitrogen (which may be in oxide form), oxygen , or sulfur (which may be in mono- or di-oxide form). Examples of the heterocycles include those mentioned above, and also pyrrole, imidazole, pyrazole, pyrimidine, pyrazine, pyridazine, indole, isothiazole, oxazole, isoxazole and triazole.

Preferably, $R^1$ is an acyl group on the 6-amino group of known penicillin derivatives or on the 7-amino group of known cephem derivatives. More preferably, $R^1$ is a group of the formula:

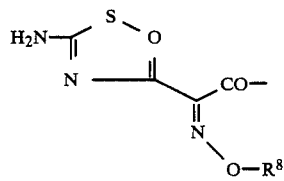

wherein Q is a nitrogen atom, CH or C—Cl, $R^6$ is hydrogen atom or a lower alkyl which may be substituted by carboxy, a group of the formula:

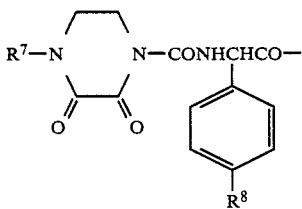

wherein R⁷ is a lower alkyl group, R⁸ is a hydrogen atom or hydroxy group, or a group of the formula:

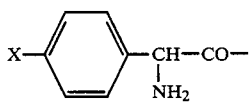

wherein X is hydrogen atom, a halogen atom or hydroxy group.

Examples of ester residues in the carboxy group which may be esterified of the symbol $R^2$ are a group of the formula:

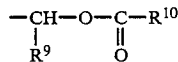

wherein $R^9$ is hydrogen atom, an alkyl, cycloalkyl or cycloalkyl-alkyl group, $R^{10}$ is hydrogen atom, or an alkyl, cycloalkyl, alkoxy, cycloalkyloxy, cycloalkyl-alkyl, alkenyloxy or phenyl group; phthalidyl, (2-oxo-5-methyl -1,3-dioxolen-4-yl)methyl, an alkoxyalkyl, an alkylthioalkyl, tert-butyl, 2,2,2-trichloroethyl, benzyl, p-methoxybenzyl, p-nitrobenzyl, benzhydryl, trityl or trimethylsilyl. In the above formula, the alkyl group of $R^9$ and $R^{10}$, and the alkyl group in the alkoxyalkyl or alkylthioalkyl group as the ester residue may be a $C_{1-6}$ straight-chain or branched-chain alkyl group such as methyl, ethyl, propyl, isopropyl, butyl or 2,2-dimethylpropyl; the cycloalkyl group and the cycloalkyl group in the cycloalkyloxy or cycloalkyl-alkyl group may be a $C_{3-7}$ cycloalkyl group such as cyclopropyl, cyclobutyl, cyclopentyl, cyclohexyl or cycloheptyl. The alkoxy group of $R^{10}$, and the alkoxy group in the alkoxyalkyl group as the ester residue may be a $C_{1-10}$ straight-chain or branched-chain alkoxy group such as methoxy, ethoxy, propoxy, isopropoxy, butoxy, hexyloxy or decyloxy. Also, the alkenyloxy group of $R^{10}$ may be a $C_{2-7}$ straight-chain or branched-chain alkenyloxy group such as allyloxy. The especially preferred ester residues are the group which can give biologically unstable ester derivatives suitable for oral administration; such as acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl or (2-oxo-5-methyl -1,3-dioxolen-4-yl)methyl.

The lower alkyl group of $R^3$, $R^4$, $R^5$, $R^6$ and $R^7$ in the above formula may be a straight-chain or branched-chain $C_{1-6}$ alkyl group, such as methyl, ethyl, propyl, isopropyl, butyl, isobutyl, tert-butyl, pentyl or hexyl. Preferable examples of the lower alkyl groups substituted by carboxyl of $R^6$ are carboxymethyl and 1-carboxy-1-methylethyl.

With regards in the symbol A in the above formula, the aromatic heterocycle in the optionally substituted bivalent aromatic heterocyclic group which is bonded on a ring-constituting carbon atom with the adjacent sulfur atom may be a five- or six- membered aromatic heterocycle containing 1 to 4 hetero atoms of nitrogen, oxygen and sulfur atoms, such as a bivalent group derived from thiazole, isothiazole, thiadiazole, triazole, tetrazole, pyridine, pyrimidine, pyridazine, oxazole, imidazole, pyrazole, oxadiazole, thiophene, furan, isoxazole, pyrazine or triazine. Preferably, the aromatic heterocycle is a five- or six-membered heterocycle containing 1 to 4 nitrogen atoms, such as tetrazole, 1,3,4-triazole, pyridazine, pyrimidine or pyridine; or a five-membered heterocycle containing 1 to 2 nitrogen atoms and one sulfur atom, such as 1,3,4-thiadiazole, 1,2,4-thiadiazole, thiazole or isothiazole.

These aromatic heterocyclic groups may be substituted by cyano, amino, a $C_{1-4}$ alkyl (such as methyl, ethyl, propyl, isopropyl or butyl), a halogen (such as fluorine, chlorine or bromine), carbamoyl or a $C_{1-4}$ alkoxycarbonyl (such as methoxycarbonyl, ethoxycarbonyl, propoxycarbonyl or butoxycarbonyl). The number of such substituents is preferably 1 to 3 and a plurality of the substituents on the same heterocycle group may be the same or different.

Preferably, the moiety of

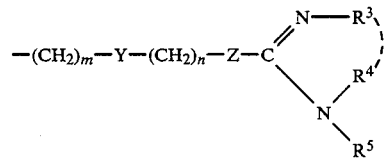

in the formula (I) is (i) where m is zero, Y is a binding arm, $R^3$, $R^4$ and $R^5$ are hydrogen, and n and Z are as defined above; (ii) where m is zero, Y is sulfur or oxygen, $R^3$ is hydrogen, methyl or cyano, $R^4$ is hydrogen or methyl, $R^5$ is hydrogen, and n and Z are as defined above, and (iii) where Y is sulfur, Z is a binding arm, n is 1, $R^3$, $R^4$ and $R^5$ are hydrogen, and m is as defined above.

Examples of the above moiety (i) are amidinomethyl, amidinoethyl amidinopropyl, amidinobutyl, guanidinoethyl or guanidinopropyl; those of the above moiety (ii) are amidinomethylthio, amidinoethylthio, amidinopropylthio, N-methylamidinomethylthio, N,N-dimethylamidinomethylthio or N-cyanoamidinomethylthio; and those of the above moiety (iii) are amidinomethyl-thiomethyl or amidinomethylthioethyl.

The salts of the compounds (I) are preferably pharmacologically acceptable salts, such as the salts with inorganic bases, organic bases, inorganic acids, organic acids, or basic or acidic amino acids. Examples of the inorganic bases which can be used to form the salt are an alkali metal (such as sodium or potassium) and an alkaline earth metal (such as calcium or magnesium); examples of the organic bases are trimethylamine, triethylamine, pyridine, picoline, N,N-dibenzylethylenediamine, ethanolamine, diethanolamine, trishydroxymethylaminomethane and dicyclohexylamine; examples of the inorganic acids are hydrochloric acid, hydrobromic acid, sulfuric acid, nitric acid and phosphoric acid; examples of the organic acids are formic acid, acetic acid, trifluoroacetic acid, oxalic acid, tartaric acid, maleic acid, methanesulfonic acid, benzenesulfonic acid and p-toluenesulfonic acid; examples of the basic or acidic amino acids are arginine, lysine, ornithine, aspartic acid and glutamic acid. Among these salts, the salts with the bases (i.e., the salts with inorganic bases, organic bases and basic amino acids) mean salts derivable in case there is(are) acid group(s) e.g. carboxy group on the substituent $R^1$ or A of the compound (I), and the salts with the acids (i.e., the salts with inorganic acids, organic acids and acidic amino acids) mean salts derivable in case there is(are) basic group(s) e.g. amino group on the substituent $R^1$ or A of the compound (I).

The compounds (I) or salts thereof of the invention are valuable antibiotics showing excellent antibacterial activities against Gram-positive and Gram-negative bacteria including clinically isolated strains and can be safely used as an antibacterial agent for treating or preventing infections caused by various bacteria in man or domestic animals.

Further, the compounds (I) or salts thereof as bactericides can be added to feeds for animals. They can be also used as disinfectants for removing harmful bacteria from medical or dental instruments.

The compounds (I) or salts thereof may be used in preparations such as capsules, tablets or injectable solutions (e.g., solutions, suspensions or emulsions) in which the above active ingredients alone or their combination with other active ingredients are formulated if necessary in an admixture with necessary carriers or excipients and other auxiliary agents such as stabilizing agents or dispersing agents. These preparations may be administered parenterally (e.g., by intravenous or intramascular injection) or orally.

Parenteral preparations may be provided in ampules or vessels containing antiseptics. Parenteral preparations may be suspensions,, solutions or emulsions in oily or aqueous media, with which known additives such as a suspending agent, a stabilizing agent and/or a dispersing agent may be suitably included. Also, the compounds (I) or salts thereof may be provided as powders which are dissolved in a suitable solvent, e.g., sterilized water free from pyrogens, just before use.

Oral preparations may be tablets, capsules or powders. Suitable agents to formulate such dosage forms are binders such as syrup, arabic gum, gelatin, sorbitol, tragacanth gum or poly-vinylpyrrolidone; fillers such as lactose, sugars, corn starch, calcium phosphate, sorbitol or glycine; lubricants such as magnesium stearate, talc, polyethyleneglycol or silica; disintegrators such as potato starch; and wetting agents such as sodium lauryl sulfate. Tablets or powders may be put into a film coating by the methods known per se. Liquid preparations such as aqueous or oily suspensions, solutions, emulsions, syrups or elixirs may be used for oral purpose. The above mentioned preparations may include other conventional additives known in the art. Also it is possible to make broader spectrum antibacterical preparations in an admixture with other active ingredients (e.g., β-lactam antibiotics).

The compounds or salts thereof can be used as therapeutic agents for infections, e.g., to treat or prevent respiratory tract infections, urinary tract infections, pyogenic infections, biliary infections, intestinal infections, gyneco-obstetrical infections, ear, nose and throat infections or surgical infections.

Daily dose of the compound (I) or salt thereof may depend upon the conditions and weights of the patients, administration methods and so forth. For parenteral administration such as intravenous or intramascular injection, it is suitably in the range of about 0.5 to 80 mg of the active ingredient (the compound (I) or salt thereof), preferably about 1 to 40 mg per kg of adult's body weight in two or four divided doses per day. For oral administration, it is suitably in the range of about 5 to 100 mg of the active ingredient (the compound (I) or salt thereof) per kg of adult's body weight in one to three divided doses per day.

The compounds (I) or salts thereof may be produced in accordance with the methods known per se (e.g., the method described in Japanese Patent Unexamined Publication No. Sho 59(1984)-53492). Further, they may be produced by Preparation Methods 1 and 2 as stated below.

Preparation Method 1

The compound (I) or a salt thereof may be produced by reacting a compound of the general formula (II)

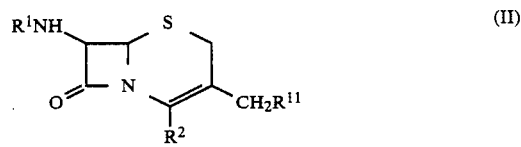
(II)

wherein $R^1$ and $R^2$ have the same meanings as defined above, and $R^{11}$ is hydroxy, an acyloxy or a halogen, or salt thereof with a compound of the general formula (III)

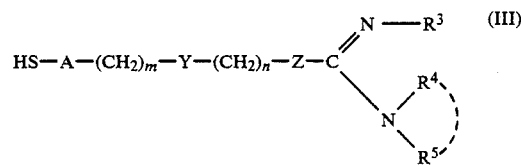
(III)

wherein the symbols have the same meanings as above, or a salt thereof, and if necessary removing the protecting group.

When the compounds (II) or (III) or salts thereof contain reactive groups such as amino, hydroxy and carboxy, these groups may be protected by protecting groups as stated below.

The salts of the compounds (II) are e.g., those with bases which can accelerate the reaction, neutralize a resulting acid through the reaction or are able to assist in dissolving the materials. Examples of the bases are tertiary amines such as triethylamine, tributylamine and diisopropylethylamine, or alkali metal hydrogen carbonates such as sodium hydrogen carbonate and potassium hydrogen carbonate. These bases may be added to the reaction mixture together with the compound (II) for the purpose stated above, preferably in an amount equal to about 1 to 5 mols to the compounds (II). The salts of the compounds (III) are e.g., the inorganic acid addition salts such as the hydrochloride, hydrobromide, sulfate, nitrate and phosphate, or the organic acid addition salts such as the formate, acetate, trifluoroacetate, methanesulfonate and p-toluenesulfonate.

(1): $R^{11}$ being hydroxy

In the reaction, the compound (III) or salt thereof is used in an amount equal to about 1 to 10 mols, preferably about 1 to 5 mols, to one mol of the compound (II) or salt thereof. The reaction is usually conducted in an organic solvent which does not hamper the reaction. Examples of the organic solvents are amides such as formamide, dimethylformamide and dimethylacetamide; halogenated hydrocarbons such as dichloromethane, chloroform and 1,2-dichloroethane; ethers such as diethyl ether, tetrahydrofuran and dioxane; esters such as methyl acetate, ethyl acetate, isobutyl acetate and methyl propionate; nitriles such as acetonitrile and propionitrile; nitro compounds such as nitromethane and nitroethane; ketones such as acetone and methyl ethyl ketone and aromatic hydrocarbons such as benzene and toluene. These solvents may be used singly or in a mixture of two or more kinds thereof at suitable ratios. Preferable solvents are dichloromethane, tetrahydrofuran, acetnitrile, formamide, dimethylformamide or the like, or mixtures of dimethylformamide and acetonitrile, dichloromethane and acetnitrile, or dichloromethane and tetrahydrofuran.

To accelerate the reaction, it is possible to use, e.g., cyclic phosphorous compounds disclosed in Japanese Unexamined Patent Publication No. Sho 58(1983)-124793, or phosphorous esters. Specifically the cyclic phosphorous compounds are represented by the general formula (IV):

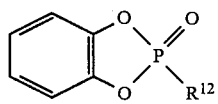
(IV)

in which $R^{12}$ is phenyl or a lower alkoxy group.

Examples of the lower alkoxy groups as $R^{12}$ of the general formula (IV) are $C_{1-4}$ alkoxy groups such as methoxy, ethoxy, propoxy, butoxy and isobutoxy. Preferable cyclic phosphorous compounds (IV) are methyl o-phenylenephosphate, ethyl o-phenylenephosphate and 2-phenyl-1,3,2-benzodioxaphosphole-2-oxide. The compound (IV) is used in the range equal to about 1 to 10 mols, preferably about 1 to 6 mols, to one mol of the compound (II) or salt thereof. When the compound (IV) is used, it is preferred that the compound (II) or salt thereof, the compound (III) or salt thereof and the compound (IV) are allowed to react in the above mentioned organic solvent. Specifically, the reaction may be achieved by mixing the compound (II) or salt thereof and the compound (III) or salt thereof in an organic solvent, to which the compound (IV) or its solution in an organic solvent is added, or by mixing the compound (III) or salt thereof and the compound (IV) in an organic solvent to, which the compound (II), salt thereof or its solution in an organic solvent is added.

The reaction temperature is usually in the range from about $-80°$ C. to $60°$ C., although it depends upon the amounts or kinds of the compounds (II) or their salts, the compounds (III) or their salts, the cyclic phosphorous compounds (IV), the organic solvents and the bases. The reaction will be completed between one minute and 24 hours.

(2): $R^{11}$ being acyloxy groups

Such acyloxy groups as acetoxy, acetoacetoxy and dichloroacetoxy are usable.

In the reaction, the compound (III) or salt thereof is usually used in an amount equal to about 1 to 5 mols, preferably about 1 to 3 mols, to one mol of the compound (II) or salt thereof. The reaction is usually conducted in water, a mixed solvent of water and an organic solvent mixable with water, or an organic solvent which does not interfere with the reaction.

When the reaction is conducted in water, or a mixed solvent of water and an organic solvent mixable with water (e.g., acetone, methanol, ethanol or acetonitrile), it is advantageous to be at a pH of between 2 to 8, preferably around neutral pH, i.e., 5 to 8. The reaction is conducted at a temperature between about $10°$ C. to $100°$ C., preferably about $30°$ C. to $80°$ C. The reaction time is usually from 10 minutes to 70 hours, depending upon the reaction temperature.

On the other hand, when an organic solvent is used, the reaction may be conducted in the presence of an acid, an acid's adduct, or water and a halogenated phosphorus compound. Preferable examples of the acids are boron trifluoride and methanesulfonic acid; preferable one of the acid's adduct is boron trifluoride etherate, and preferable examples of the halogenated phosphorus compounds are pyrophosphoryl tetrachloride and dichlorophosphoric acid. Also, the organic solvents are preferred to be ethers, halogenated hydrocarbons, ketones and nitriles as mentioned above. The reaction is conducted at a temperature of $-40°$ C. to $100°$ C., preferably $-20°$ C. to $80°$ C. and will complete from 10 minutes to 70 hours, depending upon the reaction temperature.

(3): $R^{11}$ being halogen atom

Preferable solvents in the reaction are the above mentioned ethers, esters, halogenated hydrocarbons, aromatic hydrocarbons, amides, ketones and nitriles, or water or alcohols such as methanol or ethanol. The compound (III) or salt thereof is usually used in an amount equal to about 1 to 5 mols, preferably about 1 to 3 mols, to one mol of the compound (II) or salt thereof. The reaction is conducted at a temperature of about $-10°$ C. to $100°$ C., preferably about $20°$ C. to $60°$ C. The reaction time is usually 30 minutes to 15 hours, preferably 1–5 hours. It is possible to conduct the reaction in the presence of a dehydrohalogenating agent in order to accelerate the reaction. Examples of the dehydrohalogenating agents are inorganic bases such as sodium carbonate, potassium carbonate, sodium hydrogen carbonate and potassium hydrogen carbonate; tertiary amines such as triethylamine, tripropylamine, tributylamine, diisopropylethylamine, cyclohexyldimethylamine, N,N-dimethylaniline, N-methylpiperidine, N-methylpyrrolidine and N-methylmorpholine; and alkylene oxides such as propylene oxide and epichlorhydrin. Also, the compound (II) itself may be used as the dehydrohalogenating agent. In such case, the compound (II) or salt thereof is used in an amount of two or more moles, to one mole of the compound (III).

The halogen of $R^{11}$ includes chlorine, bromine and iodine, among which iodine is preferable. The compound (II) of $R^{11}$ being iodine may be easily produced by the method described in Japanese Unexamined Patent Publication No. Sho 58(1983)-57390 and an analog one thereto.

Preparation Method 2

The compound (I) or a salt thereof may be also produced by reacting a compound of the general formula (V):

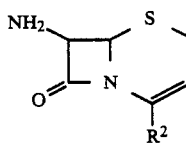 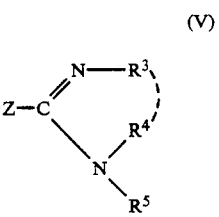 (V)

wherein the symbols have the same meanings as defined above, or a salt thereof, with a compound of the general formula (VI):

$$R^1OH \qquad (VI)$$

wherein the symbol has the same meaning as defined above, or its reactive derivative at the carboxy group, and if necessary removing the protecting group.

When an amino group exists as the substituent of $R^1$ in the formula (VI), it is preferable that it be protected by a protecting group. The protecting groups for the amino group may be suitably utilized from those used in β-lactam and peptide fields, but are preferably formyl, chloroacetyl, tert-butoxycarbonyl, benzyloxycarbonyl, p-methoxybenzyloxycarbonyl, p-nitrobenzyloxycarbonyl, 2-trimethylsilylethoxycarbonyl, 2,2,2-trichloroethoxycarbonyl, trityl or like group. When there exists a hydroxy group, it is also preferably protected by such group as a chloroacetyl, benzyl, p-nitrobenzyl, methylthiomethyl, trimethylsilyl, tert-butyldimethylsilyl, 2-tetrahydropyranyl, 4-methoxy-4-tetrahydropyranyl or like group. Further, when there is a carboxy group it is preferred that it be protected by such a group as benzyl, benzhydryl, trityl, p-methoxybenzyl, p-nitrobenzyl, tert.-butyl or like group.

The salts of the compounds (V) may be the ones with bases which are similar to those used for the salts of the compounds (II) as mentioned above. Also the base may be added together with the compound (V) and usually in an amount equal to about 1 to 10 mols, preferably about 1 to 5 mols, relative to the compound (V).

The reactive derivatives at the carboxy group of the compound (VI) may include acid halides, acid anhydrides, active amides, active esters and active thioesters which can be prepared in accordance with the conventional methods. Specifically, such reactive derivatives are as follows.

(1) Acid halides:
Acid chloride, acid bromide or like are usable.

(2) Acid anhydrides:
Mixed anhydrides with mono-lower alkyl carbonate are usable.

(3) Active amides:
Amides with pyrazole, imidazole, 4-substituted imidazole, dimethylpyrazole, benzotriazole, and like compounds are usable.

(4) Active esters
Esters such as methoxymethyl ester, benzotriazolyl ester, 4-nitrophenyl ester, 2,4-dinitrophenyl ester, trichlorophenyl ester, pentachlorophenyl ester and like ester, and esters with 1-hydroxy-1H-2-pyridone, N-hydroxysuccimide, N-hydroxyphthalimide and like compounds are usable.

(5) Active thioesters
Thioesters with heterocycle thiols such as 2-pyridylthiol and 2-benzothiazolylthiol are usable.

In the reaction, the compound (VI) or its reactive derivative at the carboxy group is used in an amount equal to 1 or more mols, preferably about 1 to 4 mols, to 1 mol of the compound (V) or salt thereof. The reaction is usually conducted in a solvent. Examples of the solvents are ketones such as acetone; ethers such as tetrahydrofuran and dioxane; nitriles such as acetonitrile; halogenated hydrocarbons such as dichloromethane, chloroform and 1,2-dichloroethane; esters such as ethyl acetate; and amides such as dimethylformamide and dimethylacetamide, which may be used singly or in an admixture at an optional ratio. When the compound (VI) is used in free form or as a salt, it is preferable that the reaction be conducted in the presence of a condensing agent. Examples of the condensing agents are N,N-dicyclohexylcarbodiimde, N-cyclohexyl-N-morpholinocarbodiimide, N-cyclohexyl-N-(4-diethylaminocyclohexyl)carbodiimide and N-ethyl-N-(3-dimethylaminopropyl)carbodiimide. The reaction may be also conducted in the presence of a base, such as alkali metal carbonates (e.g., sodium carbonate, potassium carbonate, sodium hydrogen carbonate and potassium hydrogen carbonate), tertiary amines (e.g., triethylamine, tributylamine, N-methylmorpholine, N-methylpiperidine and N,N-dimethylaniline) and pyridines (e.g., pyridine, picoline, lutidine and collidine). These bases can act to accelerate the reaction, neutralize the resulting acid or make the raw materials easily soluble, and are usually used in an amount equal to about 0.01 to 10 mols, preferably 0.1 to 5 mols, relative to the compound (V) or salt thereof. The reaction temperature is not limitative but usually in the range of $-30°$ C. to 50° C. The reaction time is about several minutes to several tens hours (e.g., 5 minutes to 30 hours).

The reaction products as obtained by the above mentioned Preparation Method 1 or 2 may be isolated and purified by known means, such as solvent extraction, change of acidity or alkalinity, phase transfer, salting out, crystallization, recrystallization or chromatography. Also, the protecting group if it is included in the reaction product is removed by the conventional method as necessary, to obtain the compound (I) or salt thereof. Protecting groups for amino, hydroxy and carboxy groups have been well studied in the field of synthesis of 8-lactams and peptides, and hence protection and de-protection methods have been established. For example, the de-protection method may be suitably selected from known methods using acids, bases, hydrazines, reduction or sodium N-methyldithiocarbamate.

The resulting compound when it is in free acid or free base form may be converted into the corresponding pharmacologically acceptable salt or ester and that when it is in its salt or ester form may be also converted into the corresponding free acid or free base. These conversions may be conducted before or after the removal of the protecting group.

By the above mentioned Preparation Methods 1 and 2, the compound (I) (syn[Z]-isomer) may be mixed with the anti[E]-isomer, according to circumstances. To isolate the desired syn-isomer (i.e., of the compound (I) or salt thereof), a the method known per se or the one analogous thereto is applicable. Examples of these methods are fractional crystallization utilizing the differential solubilities or crystallizabilities, or separation using chromatography.

Furthermore, the raw materials of the compounds (II) and salts thereof can be obtained by the methods disclosed in, e.g., Japanese Unexamined Patent Publication Nos. 53(1978)-34795 and 52(1977)-125190 and Japanese Patent Publication Nos. 53(1978)-1280 and 58(1983)-58353 or the ones analogous thereto. Also, the compound (III) can be obtained in accordance with a method similar to that disclosed in Journal of the Chemical Society 1393, (1948) or the method shown by Reference Examples as stated herein after or the one analogous thereto. The compound (VI) and reactive derivatives thereof can be produced by the method known per se.

(EXAMPLES AND REFERENCE EXAMPLES)

This invention is illustrated in further detail in the Reference Examples and Examples, which are only examples, and do not limit this invention. Modification within the scope of this invention are permissible.

Elution in a column chromatography in the Reference Examples and Examples was conducted while monitoring with TLC (Thin Layer Chromatography). In the TLC monitoring, the TLC plate used was 60F$_{254}$ manufactured by Merck Co., the developing solvent was the same as the one used for eluting in the column chromatography, and the detection was conducted with a UV detector. The silica gel for the column was Kieselgel 60 manufactured by Merck Co. (West Germany), (70-230 mesh). "Sephadex" is a product of Pharmacia Fine Chemicals Co. (Sweden). XAD-II resin is a product of Rohm & Haas Co. (U.S.A.). HP-20 resin is a product of Mitsubishi Chemical Industries Ltd. (Japan). NMR spectra were measured using tetramethylsilane as an internal or external standard with a spectrometer EM390 (90 MHz) or Gemini 200 (200 MHz) and all $\delta$ values are expressed in ppm. The value shown in ( ) for a mixed solvent is a mixing ratio in volume of constituent solvents. The percent(%) for a mixed solvent indicates the percent by volume. The percent(%) means w/w % unless otherwise specified. The symbols in Reference Examples and Examples have the following meaning.
s: singlet
d: doublet
t: triplet
q: quartet
ABq: AB type quartet
dd: double doublet
m: multiplet
br.: broad
J: coupling constant
sh: shoulder (REFERENCE EXAMPLE)

Reference Example 1

In 100 ml of water was suspended 10 g of 7-aminocephalosporanic acid (hereinafter abbreviated as "7-ACA"). The pH of the suspension was maintained at 12.5 to 13.4 by gradual addition of 2N-sodium hydroxide solution under ice-cooling and stirring. The mixture was further stirred for 2 hours, and adjusted to pH 3.4 with 4N-hydrochloric acid after confirming the disappearance of the starting material (7-ACA) by TLC. The precipitating crystals were collected by filtration, washed with water and acetone and dried over phosphorus pentoxide under reduced pressure to give 5.4 g of 7$\beta$-amino-3-hydroxymethyl -3-cephem-4-carboxylic acid as pale yellow crystals.
IR(KBr)cm$^{-1}$: 3400, 3190, 3000, 2930, 2600, 1795, 1615
Elemental analysis for $C_8H_{10}N_2O_4S \cdot \frac{1}{2}H_2O$:
Calcd.(%): C,41.33; H,4.44; N,12.05.
Found(%): C,41.29; H,4.39; N,11.84.

Reference Example 2

In 800 ml of a (1:1) mixture of water and tetrahydrofuran (hereinafter abbreviated as "THF") was suspended 16.9 g of 7$\beta$-amino-3-hydroxymethyl-3-cephem-4-carboxylic acid, and 27.72 g of sodium hydrogencarbonate were added under ice-cooling and stirring. Then, 29.4 g of 2-(2-chloroacetamidothiazol-4-yl)-(Z)-2-methoxyiminoacetyl chloride hydrochloride were gradually added to the mixture and stirred for 30 minutes. The reaction mixture was shaken with 150 ml of water and 200 ml of ethyl acetate. The aqueous layer was taken and adjusted to pH 7.0 with 1N-hydrochloric acid under stirring and ice-cooling. To the mixture was gradually added 18.9 g of sodium N-methyldithiocarbamate under stirring at room temperature, to remove the protecting group for amino group (monitoring with TLC).

To the reaction mixture was added 300 ml of ethyl acetate and the mixture was shaken. The aqueous layer was taken and concentrated to 70 ml under reduced pressure. The residue was subjected to a column chromatography on XAD-II (1l) being eluted with water.

The fractions containing the object compound were collected and concentrated to 100 ml and, under ice-cooling and stirring, the residue was adjusted to pH 2.5 with 4N-hydrochloric acid. The separating precipitate was collected by filtration, washed with 100 ml of water, 50 ml of ethyl acetate and 50 ml of THF, and then dried under reduced pressure to give 19.3 g of 7$\beta$-[2-(2-aminothiazol-4-yl)-(Z)-2-methoxyiminoacetamido]-3-hydroxymethyl-3-cephem-4-carboxylic acid.
IR(KBr)cm$^{-1}$: 3330, 3250, 2930, 1760, 1655
NMR(d$_6$-DMSO)$\delta$: 3.84(3H,s), 4.25(2H,s), 6.73(1H,s)
Elemental analysis for $C_{14}H_{15}N_5O_6S_2 \cdot \frac{1}{2}H_2O$:
Calcd.(%) : C,39.81; H,3.82; N,16.58.
Found(%) : C,39.73; H,3.74; N,16.39.

To a solution of 1.85 g of tri-n-butylamine in 150 ml of methanol was added 4.13 g of the compound obtained as above, under stirring at $-20°$ C. The mixture was stirred to become a clear solution. After removing methanol under reduced pressure, the residue was added with 200 ml of dry dichloromethane. Then, the solvent was distilled off under reduced pressure and the residue was dried to give n-butylammonium 7$\beta$-[2-(2-aminothiazol-4-yl)-(Z)-2-methoxyiminoacetamido]-3-hydroxymethyl-3-cephem-4-carboxylate as a foam closely quantitatively.

In a similar manner as above were obtained the following compounds.
(a) 7$\beta$-[2-(2-Aminothiazol-4-yl)-(Z)-2-ethoxyiminoacetamido]3-hydroxymethyl-3-cephem-4-carboxylic acid
IR(KBr)cm$^{-1}$: 1765, 1665

NMR(d₆-DMSO)δ: 1.23(3H,t,J=7 Hz), 4.11(2H,q,J=7 Hz), 4.26(2H,s), 6.72(1H,s)

(b) Tri-n-butylammonium 7β-[2-(2-aminothiazol-4-yl)-(Z)-2-ethoxyiminoacetamido]-3-hydroxymethyl-3-cephem-4-carboxylate (a foam powder)

Reference Example 3

In 100 ml of dichloromethane were added 1.01 g of 2-(5-amino-1,2,4-thiadiazol-3-yl)-(Z)-2-methoxyiminoacetic acid, 1.03 g of dicyclohexylcarbodiimide and 0.756 g of 1-hydroxybenzotriazole monohydrate and the mixture was stirred at room temperature for 2 hours. The resultant precipitate was collected by filtration. On the other hand, 1.26 g of sodium 7β-amino-3-hydroxy-3-cephem-4-carboxylate was suspended in 25 ml of dimethylformamide (hereinafter abbreviated as "DMF") and then all of the above crystals were added to the suspension. The mixture was stirred at room temperature for 4 hours and, then, at 5° C. for 14 hours. The mixture was diluted with 30 ml of water and 100 ml of ethyl acetate and well shaken. The aqueous layer taken was concentrated to about 10 ml under reduced pressure and subjected to a column chromatography on silicagel (170 g) which was washed with acetonitrile and eluted with a (4:1) mixture of acetonitrile and water. The eluate was concentrated to 20 ml under reduced pressure. Further, the concentrate was subjected to a column chromatography on XAD-II (200 ml), washing with water and eluting with 10% aqueous ethanol. The eluate was concentrated under reduced pressure and then lyophilized to give 1.2 g of sodium 7β-[2-(5-amino-1,2,4-thiadiazol-3-yl)-(Z)-2-methoxyiminoacetoamido]-3-hydroxymethyl-3-cephem-4-carboxylate.

IR(KBr)cm⁻¹: 1760, 1665, 1600
NMR(D₂O)δ: 4.18(3H,s), 4.37(2H,s), 5.30(1H,d,J=5 Hz), 5.92(1H,d)
Elemental analysis for $C_{13}H_{13}N_6NaO_6S_2.2H_2O$:
Calcd.(%) : C,33.05; H,3.63; N,17.79.
Found(%) : C,33.09; H,3.55; N,17.61.

In a similar manner as above was obtained sodium 7β-[2-(5-amino-1,2,4-thiadiazol-3-yl)-(Z)-2-ethoxyiminoacetamido]-3-hydroxymethyl-3-cephem-4-carboxylate.

IR(KBr)cm⁻¹: 3300, 1760, 1670, 1610:
NMR(d₆-DMSO)δ: 1.26(3H,t,J=7 Hz), 3.96(2H,ABq,J=12 Hz), 4.16(2H,q,J=7 Hz), 4.92(1H,d,J=5 Hz), 5.60(1H,dd,J=5&8 Hz)
Elemental analysis for $C_{14}H_{15}N_6NaO_6S_2.2H_2O$:
Calcd.(%) : C,34.57; H,3.94; N,17.28.
Found(%) : C,34.76; H,3.84; N,17.18.

Reference Example 4

In 180 ml of water was suspended 5.756 g of 7β-amino3-hydroxymethyl-3-cephem-4-carboxylic acid. When the suspension was adjusted to pH 7.6 by addition of 1N sodium hydroxide under ice-cooling, the compound was completely dissolved. To this solution were added 11.965 g of S-(2-benzothiazolyl) 2-(2-aminothiazol-4-yl)-(Z)-2-[1-(tert-butoxycarbonyl)-1-methylethoxyimino]thioacetate and 220 ml of THF. The mixture was stirred at room temperature for 24 hours and THF was distilled off under reduced pressure. The remaining aqueous solution was washed with 200 ml of ethyl acetate. The aqueous layer was concentrated to 100 ml under reduced pressure, the remaining solution was subjected to a column chromatography on HP-20 (250 ml) being washed with 1l of water and eluted with 2.5l of 10% aqueous ethanol. The eluate was concentrated to 200 ml, and filtered, and the filtrate was lyophilized to give 9.3 g of sodium 7β-[2-(2-aminothiazol-4-yl)-(Z)-2-[1-(tert-butoxycarbonyl)-1-methylethoxyimino)acetamido]]-3-hydroxymethyl-3-cephem-4-carboxylate as pale yellow powders.

IR(KBr)cm⁻¹: 3300, 2975, 2925, 1750, 1670, 1600:
NMR(D₂O)δ: 1.58(9H,s), 1.67(6H,s), 3.66(2H,ABq, J=18 Hz), 4.37(2H,s), 5.32(1H,d,J=5 Hz), 5.93(1H,d, J=5 Hz), 7.15(1H,s)
Elemental analysis for $C_{21}H_{26}N_5O_8NaS_2.2.5H_2O$:
Calcd.(%) : C,41.44; H,5.13; N,11.51.
Found(%) : C,41.39; H,4.99; N,11.65.

In a similar manner as above was obtained sodium 7β-[2-(2-aminothiazol-4-yl)-(Z)-2-(tert-butoxycarbonylmethoxyimino)acetamido]-3-hydroxymethyl-3-cephem-4-carboxylate.

IR(KBr)cm⁻¹: 1760, 1660(sh), 1600, 1525
NMR(D₂O)δ: 1.68(9H,s), 3.74(2H,ABq,J=18 Hz), 4.47(2H,s), 4.93(2H,s), 5.04(1H,d,J=5 Hz), 6.02 (1H,d,J=5 Hz), 7.28(1H,s)
Elemental Analysis for $C_{19}H_{22}N_5NaO_8S_2.2 5H_2O$:
Calcd.(%) : C,39.31; H,4.69; N,12.06.
Found(%) : C,39.25; H,4.45; N,12.20.

Reference Example 5

In 500 ml of a (1:1) mixture of water and THF was suspended 11.9 g of 7β-amino-3-hydroxymethyl-3-cephem-4-carboxylic acid, and 19.4 g of sodium hydrogencarbonate was added under ice-cooling and stirring. To the suspension was added 20.6 g of 2-(2-chloroacetamidothiazol-4-yl)-(Z)-2-methoxyiminoacetyl chloride hydrochloride, followed by stirring for 30 minutes. The reaction mixture was shaken with 100 ml of water and 150 ml of ethyl acetate. The aqueous layer was taken and adjusted to pH 7.0 with 1N-hydrochloric acid under ice-cooling and stirring. To the mixture was gradually added 12.0 g of sodium N-methyldithiocarbamate at room temperature under stirring to remove the amino group. After shaking with 200 ml of ethyl acetate, the aqueous layer was taken and concentrated to 50 ml under reduced pressure. The residue was subjected to a column chromatography on XAD-II (1.2l) eluting with water. The fractions containing the objective compound were collected, concentrated under reduced pressure, and then lyophilized to give 12.4 g of sodium 7β-[2-(2-aminothiazol-4-yl)-(Z)-2-methoxyiminoacetamido]-3-hydroxymethyl-3-cephem-4-carboxylate as pale yellow powders.

IR(KBr)cm⁻¹: 1760, 1655, 1600, 1530
NMR(d₆-DMSO)δ: 3.85(3H,s), 4.02(2H,ABq,J=13 Hz), 4.93 (1H,d,J=5 Hz), 5.55(1H,dd,J=5&8 Hz), 6.73(1H,s), 7.21 (2H,br.s), 9.48(1H,d,J=8 Hz)
Elemental analysis for $C_{14}H_{14}N_5NaO_6S_2.1H_2O$:
Calcd.(%) : C,37.08; H,3.56; N,15.45.
Found(%) : C,37.40; H,3.46; N,15.63.

In a similar manner as above was obtained the following compound:
sodium 7β-[2-(2-aminothiazol-4-yl)-(Z)-2-ethoxyiminoacetamido]-3-hydroxymethyl-3-cephem-4-carboxylate.

IR(KBr)cm⁻¹: 1760, 1660, 1600, 1530
NMR(d₆-DMSO)δ: 1.23(3H,t,J=7 Hz), 4.03(2H,ABq,J=13 Hz), 4.10(2H,q,J=7 Hz), 4.94(1H,d,J=5 Hz), 5.58(1H,dd,J=5&8 Hz), 6.69(1H,s), 7.19(2H,br.s), 9.43(1H,d,J=8 Hz)

Reference Example 6

A mixture of 980 mg of 1-(2-aminoethyl)-5-mercapto-1H-tetrazole, 696mg of S-methylisourea sulfate, 2.31 ml of triethylamine and 60 ml of DMF was stirred at 70° C. for 17 hours. Then the solvent was distilled off and the residue was purified by a column chromatography (silica gel=150 g; acetonitrile - water=7:1, then 5:1) to give 335mg of 1-(2-guanidinoethyl)-5-mercapto-1H-tetrazole as colorless crystals.

IR(KBr)cm$^{-1}$: 3320, 3150, 1660, 1630, 1430, 1405
NMR(d$_6$-DMSO)δ: 3.4–3.7(2H,m), 4.23(2H,t,J=6 Hz), 7.0–7.8 (4H,m)

Reference Example 7

To a solution of 1.50 g of 2,5-dimercapto-1,3,4-thiadiazole and 4.2 ml of triethylamine in 30 ml of DMF was added 1.29 g of α-chloroacetamidine hydrochloride at room temperature under stirring. Further, the mixture was stirred for 2.5 hours at room temperature and concentrated under reduced pressure. The residue was subjected to a column chromatography on silica gel (100 g), eluting with a (4:1) mixture of acetonitrile and water. The pertinent fractions were collected and concentrated under reduced pressure, and the concentrate was subjected to a column chromatography on XAD-II (450 ml) being washed with water, and eluted with 10% aqueous ethanol. After concentrating, the precipitating crystals were filtered to give 755mg of 2-amidinomethylthio-5-mercapto-1,3,4-thiadiazole as colorless crystals, mp: 184°–187° C.

IR(KBr)cm$^{-1}$: 3330, 3120, 1675, 1650
NMR(d$_6$-DMSO)δ: 2.93(2H,t,J=7 Hz), 4.50(2H,t,J=7 Hz), 8.91 (4H,br.)
Elemental analysis for C$_4$H$_8$N$_6$S.0.1H$_2$O:
Calcd.(%) : C,27.61; H,4.75; N,48.30.
Found(%) : C,27.52; H,4.69; N,48.38.

Reference Example 8

To a solution of 1.94 g of dipotassium cyanodithioimidocarbonate in 16 ml of 50% aqueous ethanol was added 321 mg of sulfur, followed by stirring for 3 hours at room temperature. The mixture was filtered and to the filtrate was added 1.29 g of o-chloroacetamidine hydrochloride. The mixture was stirred for an hour at room temperature and concentrated under reduced pressure. The precipitating crystals were collected by filtration and washed with cold water and ethanol to give 1.14 g of 3-amidinomethylthio-5-mercapto-1,2,4-thiadiazole as pale yellow crystals, mp 158°–163° C. (decomp.).

IR(KBr)cm$^{-1}$: 3270, 3060, 1690, 1430, 1420
NMR(d$_6$-DMSO)δ: 4.07(2H,s), 8.66(2H,br.), 9.10(2H,br.)
Elemental analysis for C$_4$H$_6$N$_4$S$_3$. 0.4H$_2$O:
Calcd.(%) : C,22.50; H,3.21; N,26.24.
Found(%) : C,22.63; H,3.27; N,26.36.

Reference Example 9

3-Amidinomethylthio-6-mercaptopyridazine hydrochloride as yellow crystals, mp 205°–210° C. (decomp.), was obtained in a manner similar to that described in Reference Example 7.

IR(KBr)cm$^{-1}$: 3330, 3230, 3050, 2860, 1690, 1645, 1590, 1530
NMR(d$_6$-DMSO)δ: 4.13(2H,s), 7.32(1H,d,J=9 Hz), 7.50(1H, d,J=9 Hz), 8.8–9.5(3H,br.)
Elemental analysis for C$_6$H$_8$N$_4$S$_2$.HCl.0.4H$_2$O:
Calcd.(%) : C,29.98; H,3.94; N,23.31.
Found(%) : C,30.02; H,3.79; N,23.09.

Reference Example 10

2-(2-Guanidinoethylthio-5-mercapto-1,3,4-thiadiazole hydrochloride as colorless crystals was obtained in a manner similar to that described in Reference Example 6.

IR(KBr)cm$^{-1}$: 3330, 3180, 3130, 2980, 2800, 1670, 1640, 1600
NMR(d$_6$-DMSO)δ: 3.1–3.6(4H,m), 7.37(3H,br.), 7.85–8.1(1H,m)

Reference Example 11

In 30 ml of ethanol was suspended 2.25 g of 2,5-dimercapto-1,3,4-thiadiazole, and 30 ml of 1N-sodium hydroxide solution was added to the suspension. The mixture was stirred at room temperature for 30 minutes. To the mixture was added 2.36 g of N,N-dimethylchloroacetamidine. The mixture was stirred at room temperature for an hour and concentrated under reduced pressure. The precipitating crystals were collected by filtration and washed with cold water and then a (1:1) mixture of methanol and ethyl ether to obtain 1.87 g of 2-(N,N-dimethylamidinomethylthio)-5-mercapto-1,3,4-thiadiazole as colorless crystals (mp 95°–97° C.).

IR(KBr)cm$^{-1}$: 3380, 3080, 1670, 1610, 1340
NMR(d$_6$-DMSO)δ: 4.16(2H,s), 8.90(1H,br)
Elemental analysis for C$_6$H$_{10}$N$_4$S$_3$.1H$_2$O:
Calcd.(%) : C,28.55; H,4.79; N,22.20.
Found(%) : C,28.68; H,4.57; N,22.28.

Reference Example 12

1-(3-Guadininopropyl)-5-mercapto-1H-tetrazole as colorless crystals was obtained in a manner similar to that described in Reference Example 6.

IR(KBr)cm$^{-1}$: 3320, 3150, 1690, 1640, 1610
NMR(d$_6$-DMSO)δ: 1.94(2H,quintet,J=7 Hz), 3.13(2H,q,J=7 Hz), 4.17(2H,t,J=7 Hz), 7.22(3H,br.), 7.6–7.9(1H,m)

Reference Example 13

In 30 ml of ethanol was suspended 2.25 g of 2,5-dimercapto-1,3,4-thiadiazole, and 30 ml of 1N-sodium hydroxide solution was added to the suspension under ice-cooling and stirring. To the mixture was further added 2.33 g of 2-(chloromethyl)imidazoline hydrochloride, and the mixture was stirred at room temperature for 90 minutes and concentrated under reduced pressure. The concentrate was adjusted to pH 4.8 and washed with ethyl acetate. The aqueous layer was concentrated and subjected to a column chromatography on XAD-II (300 ml), being washed with water and eluted with 10% aqueous ethanol. The eluate was evaporated to dryness under reduced pressure. To the residue were added 50 ml of ethanol and 5 ml of conc hydrochloric acid, and the resultant was stirred. The precipitating crystals were collected by filtration and washed with ethanol to give 2.10 g of 2-(2-imidazolin-2-yl)methylthio-5-mercapto-1,3,4-thiadiazole hydrochloride as colorless crystals (mp 204°–209° C. decomp.).

IR(KBr)cm$^{-1}$: 3400, 3070, 2930, 2780, 1605, 1490
NMR(d$_6$-DMSO)δ: 3.87(4H,s), 4.35(2H,s), 10.65(2H,br.)
Elemental analysis for C$_6$H$_8$N$_4$S$_3$.HCl:
Calcd.(%) : C,26.81; H,3.37; N,20.84.
Found(%) : C,26.94; H,3.51; N,20.63.

Reference Example 14

In 40 ml of 50% aqueous ethanol was dissolved 2.18 g of disodium 4-cyano-3,5-dimercaptoisothiazole, to which 1.29 g of α-chloroacetamidine hydrochloride was added. The mixture was stirred for 2 hours, concentrated under reduced pressure, diluted with water and adjusted to pH 5.2. The precipitating crystals were collected by filtration and washed with water and then ethanol to give 1.23 g of 3-amidinomethylthio-4-cyano-5-mercaptoisothiazole as gray crystals (mp 198°–201° C., decomp.).

IR(KBr)cm$^{-1}$: 3250, 3070, 3040, 2220, 1680, 1500, 1325
NMR(d$_6$-DMSO)δ: 4.12(2H,s), 8.75(4H,br.)
Elemental analysis for C$_6$H$_6$N$_4$S$_3$:
Calcd.(%) : C,31.29; H,2.63; N,24.32.
Found(%) : C,30.96; H,2.62; N,24.06.

Reference Example 15

3-Amidinomethylthio-5-mercapto-4-methyl-4H-1,2,4-triazole as grayish white crystals, mp 193°–195° C. (decomp.), was obtained in a manner similar to that described in Reference Example 11.

IR(KBr)cm$^{-1}$: 3100–2900(br.), 1685, 1500, 1470, 1450
NMR(d$_6$-DMSO)δ: 3.78(3H,s), 4.38(2H,s)
Elemental analysis for C$_5$H$_9$N$_5$S$_2$.0.2H$_2$O:
Calcd.(%) : C,29.03; H,4.58; N,33.85.
Found(%) : C,29.09; H,4.49; N,33.77.

Reference Example 16

1-(4-Guanidinobutyl)-5-mercapto-1H-tetrazole as a yellowish solid was obtained in a manner similar to that described in Reference Example 6.

IR(KBr)cm$^{-1}$: 3400, 3250, 3080, 1670, 1630
NMR(d$_6$-DMSO)δ: 1.3–2.0(4H,m), 3.14(2H,q,J=6 Hz), 4.16 (2H,t,J=6 Hz), 7.23(3H,br.s), 7.73(1H,t,J=6 Hz)

Reference Example 17

2-(N-Methylamidinomethylthio)-5-mercapto-1,3,4-thiadiazole as colorless crystals was obtained in a manner similar to that described in Reference Example 11.

IR(KBr)cm$^{-1}$: 3270, 3170, 2980, 1685, 1640
NMR(d$_6$-DMSO)δ: 3.18(1H,s), 4.33(2H,s)
Elemental analysis for C$_5$H$_8$N$_4$S$_3$.0.3H$_2$O:
Calcd.(%) : C,26.60; H,3.84; N,24.82.
Found(%) : C,26.50; H,3.79; N,24.93.

Reference Example 18

4-Cyano-3-(N-methylamidinomethylthio)-5-mercaptoisothiazole as gray crystals, mp 199°–202° C. (decomp.), was obtained in a manner similar to that described in Reference Example 14.

IR(KBr)cm$^{-1}$: 3400, 3300, 3200, 3080, 2210, 1685, 1620, 1450
NMR(d$_6$-DMSO)δ: 2.82(3H,s), 4.13(2H,s), 9.07(3H,br.)
Elemental analysis for C$_7$H$_8$N$_4$S$_3$:
Calcd.(%) : C,34.40; H,3.30; N,22.93.
Found(%) : C,34.21; H,3.13; N,22.65.

Reference Example 19

In 20 ml of ethanol was suspended 1.49 g of thiazolidine -2,4-dithione, and 20 ml of 1N-sodium hydroxide solution was added under ice-cooling and stirring. To the mixture was added 1.29 g of α-chloroacetamidine hydrochloride, and the resultant was stirred at room temperature for 2.5 hours and concentrated. The precipitating crystals were collected by filtration, suspended to water, and hydrochloric acid was added to the suspension to dissolve the crystals. Thereafter this solution was subjected to a column chromatography on XAD-II (450 ml) being eluted with water. The eluate was evaporated to dryness and treated with ethanol. The resultant crystals were washed with a (1:2) mixture of ethanol and ethyl acetate to give 0.48 g of 4-amidinomethylthio-2-mercaptothiazole hydrochloride as colorless crystals. mp 178°–181° C. (decomp.)

IR(KBr)cm$^{-1}$: 3330, 3030, 2780, 1700, 1650
NMR (d$_6$-DMSO)δ: 3.84(2H,s), 7.25(1H,s), 9.05(2H,br.s), 9.28(2H,br.s)
Elemental analysis for C$_5$H$_7$N$_3$S$_3$.HCl:
Calcd (%) : C,24.84; H,3.33; N,17.38.
Found(%) : C,24.97; H,3.29; N,17.14.

Reference Example 20

4-Amidinomethylthio-6-mercaptopyrimidine hydrochloride as pale yellow crystals, mp 206°–210° C., was obtained in a manner similar to that described in Reference Example 13.

IR(KBr)cm$^{-1}$: 3300, 3200, 2830, 1680, 1590
NMR(d$_6$-DMSO)δ: 4.19(2H,s), 7.21(1H,s), 8.19(1H,s), 9.23 (4H,br.s)
Elemental analysis for C$_6$H$_8$N$_4$S$_2$.HCl:
Calcd.(%) : C,30.44; H,3.83; N,23.67.
Found(%) : C,30.53; H,3.77; N,23.41.

Reference Example 21

3-Amidinomethylthio-4-amino-5-mercapto-4H-1,2,4-triazol as gray crystals was obtained in a manner similar to that described in Reference Example 11.

IR(KBr)cm$^{-1}$: 3310, 3080, 1660, 1635, 1355
NMR(D$_2$O+DCl)δ: 4.37(2H,s)

Reference Example 22

To a suspension of 996 mg of 3-aminopropioamidine dihydrobromide in 20 ml of DMF was added 0.56 ml of triethylamine under ice-cooling and stirring, and then 684 mg of 5-mercapto-1,3,4-triadiazole-2-carboxylic acid, 756 mg of 1-hydroxybenzotriazole and 1.03 g of dicyclohexylcarbodiimide, followed by stirring at room temperature for 48 hours. The resultant precipitate was removed by filtration and the filtrate was concentrated under reduced pressure. To the residue was added ethyl acetate and dilute hydrocholic acid. After shaking, the aqueous layer was concentrated under reduced pressure. The concentrate was subjected to a column chromatography on XAD-II (400 ml) eluting with water, and the eluate was evaporated to dryness. Ethanol was added to the residue to crystallize and the crystals were washed with a (1:1) mixture of ethanol and ethyl ether to give 427 mg of 2-[N-(2-amidinoethyl)carbamoyl]-5-mercapto-1,3,4-thiadiazole hydrobromide as colorless crystals.

IR(KBr)cm$^{-1}$: 3380, 3250, 3060, 2920, 2780, 1690 1650, 1540
NMR(d$_6$-DMSO)δ: 2.65(2H,t,J=6 Hz), 3.56(2H,q,J=6 Hz), 8.78(2H,br.s), 9.07(2H,br.s), 9.23(1H,t,J=6 Hz)

Reference Example 23

3-[N-(2-Amidinoethyl)carbamoyl]-6-mercaptopyrimidine hydrobromide as yellow powders was obtained in a manner similar to that described in Reference Example 22.

IR(KBr)cm$^{-1}$: 3280, 3070, 2870, 1685, 1650
NMR(d$_6$-DMSO)δ: 2.63(2H,t,J=6 Hz), 3.4–3.7(2H,m), 7.2–8.3(3H,m), 8.61(2H,br.s), 9.05(2H,br.s), 8.90 (1H,t,J=5 Hz)

Elemental analysis for C$_9$H$_{12}$N$_4$OS.HBr:
Calcd.(%) : C,35.42; H,4.29; N,18.36.
Found(%) : C,35.36: H,4.33: N,18.39.

Reference Example 24

To a suspension of 3.0 g of 2,5-dimercapto-1,3,4-thiadiazole in 30 ml of methanol and 10 ml of water was added 10 ml of 1N sodium hydroxide solution under stirring and then 2.35 g of chloromethylcyanoamidine, followed by stirring at room temperature for 3 hours. The mixture was concentrated under reduced pressure and the residue was extracted with ethyl acetate. The extract was washed with water, dried and concentrated. The residue was subjected to a column chromatography on silica gel (100 g), being eluted with a (9:1) mixture of ethyl acetate and ethanol, to give 1.93 g of 2-cyanoamidinomethylthio-5-mercapto-1,3,4-thiadiazole as pale yellow powders.

IR(KBr)cm$^{-1}$: 3280, 3140, 2160, 1640, 1490
NMR(d$_6$-DMSO)δ: 4.03(2H,s), 8.64(2H,br.s)

Reference Example 25

4-Cyano-3-cyanoamidinomethylthio-5-mercaptoisothiazole as orange powders was obtained in a manner similar to that described in Reference Example 24.

IR(KBr)cm$^{-1}$: 3310, 3170, 2180, 1640, 1565
NMR(d$_6$-DMSO)δ: 4.06(2H,s), 8.53(2H,br.)

Reference Example 26

(a) 2,5-Dimercapto-1,3,4-thiadiazole (7.50 g) was dissolved in a mixture of 50 ml of ethanol and 50 ml of 1N-sodium hydroxide solution to which 4.15 ml of 3-bromopropionitrile was added under stirring. After stirring for 48 hours at room temperature, the mixture was concentrated under reduced pressure. The concentrate was extracted with ethyl acetate. The extract was dried over sodium sulfate and distilled off to remove the solvent. The residue was washed with ethyl ether to give 7.74 g of 2-(2-cyanoethylthio)-5-mercapto-1,3,4-thiadiazole as yellow crystals.

IR(KBr)cm$^{-1}$: 3030, 2830, 2250, 1495, 1270
NMR(d$_6$-DMSO)δ: 2.99(2H,t,J=7 Hz), 3.43(2H,t,J=7 Hz)

(b) The product in the above a) (5.0 g) was suspended in 80 ml of a (5:3) mixture of chloroform and ethanol. The suspension was saturated with hydrogen chloride and stirred at 3°–5° C. for 30 hours. The reaction mixture was evaporated to dryness. To the residue was added 100 ml of 9.5% ammoniamethanol solution, followed by stirring at room temperature for 48 hours. The mixture was distilled under reduced pressure to remove the solvent. The residue was diluted with water and concentrated again. The precipitating crystals were collected by filtration, and washed with water and ethanol to give 1.42 g of 2-(2-amidinoethylthio)-5-mercapto-1,3,4-thiadiazole as yellowish brown crystals.

IR(KBr)cm$^{-1}$: 1680, 1530, 1390, 1270, 1180
NMR(d$_6$-DMSO)δ: 2.85(2H,t,J=7 Hz), 4.41(2H,t,J=7 Hz), 8.55(2H,br.), 8.95(2H,br.)

Reference Example 27

2-(3-Amidinopropylthio)-5-mercapto-1,3,4-thiadiazole hydrochloride as yellowish brown crystals, mp 171°–174° C., was obtained in a manner similar to that described in Reference Example 26.

IR(KBr)cm$^{-1}$: 3300, 3070, 2780, 1670, 1480
NMR(d$_6$-DMSO)δ: 1.8–2.3(2H,m), 2.54(2H,t,J=7 Hz), 3.18(2H,t,J=7 Hz), 8.86(2H,br.s), 9.18(2H,br.s)

Elemental analysis for C$_6$H$_{10}$N$_4$S$_3$.HCl.1H$_2$O:
Calcd.(%) : C,24.95; H,4.54; N,19.40.
Found(%) : C,24.73; H,4.15; N,19.47.

Reference Example 28

(a) Cysteamine hydrochloride (11.36 g) was dissolved in 200 ml of an aqueous solution containing 13.4 g of potassium hydroxide, to which 12 ml of chloroacetonitrile was added dropwise. Then the mixture was stirred at room temperature for 20 minutes, and extracted with chloroform. The extract was dried over anhydrous sodium sulfate and concentrated under reduced pressure. The residue was dissolved in 100 ml of 92% aqueous ethanol, to which 24.6 ml of triethylamine was added under stirring and then 7.20 g of carbon disulfide was added dropwise. The mixture was stirred at 15° C. for an hour. Then, 12.8 g of methyl iodide was added to the mixture at the same temperature, followed by stirring for 30 minutes. The reaction mixture was diluted with 110 ml of water and 53 ml of hexane. The aqueous layer was taken, acidified with phosphoric acid and extracted with ethyl acetate. The extract was washed with an aqueous sodium chloride solution, dried over anhydrous sodium sulfate and distilled off under reduced pressure to remove the solvent. The residue was dissolved in 70 ml of ethanol, to which 35 ml of an aqueous solution containing 5.2 g of sodium azide was added. The mixture was refluxed for 2 hours and concentrated under reduced pressure. Water and ethyl acetate were added to the residue and shaken well. The aqueous layer was taken, acidified and extracted with ethyl acetate. The extract was washed with an aqueous sodium chloride solution, dried over anhydrous sodium sulfate and concentrated. The residue was subjected to a column chromatography on silica gel (250 g), being eluted with ethyl acetate to give 4.95 g of 1-(2-cyanomethylthioethyl)-5-mercapto-1H-tetrazole as an oil.

IR(Neat)cm$^{-1}$: 2930, 2230, 1490, 1390
NMR(d$_6$-DMSO)δ: 3.30(2H,t,J=6 Hz), 3.52(2H,s), 4.60(2H,t, J=6 Hz)
MS m/e: 201(M)

(b) A solution of 4.0 g of the product in the above (a) in 50 ml of chloroform and 30 ml of ethanol was saturated with hydrogen chloride under ice-cooling. The mixture was allowed to stand in a refrigerator for 2 days, and concentrated to dryness under reduced pressure. To the residue were added 20 ml of methanol and 50 ml of ammonia saturated methanol, and the whole was stirred at 37° C. for 24 hours. The reaction mixture was concentrated to dryness, and 50 ml of water was added to the residue and the whole was cooled. The resultant crystals were collected by filtration and washed with cold water to give 2.44 g of 1-(2-amidinomethylthioethyl)-5-mercapto-1H-tetrazole as yellow brown crystals. mp 201°–203° C. (decomp.)

IR(KBr)cm$^{-1}$: 3370, 3020, 1660, 1440, 1400
NMR(d$_6$-DMSO)δ: 3.04(2H,t,J=7 Hz), 3.52(2H,s), 4.37 (2H,t,J=7 Hz)

Elemental analysis for C$_5$H$_{10}$N$_6$S$_2$:

Calcd.(%) : C,27.51; H,4.62; N,38.50.
Found(%) : C,27.59; H,4.67; N,38.37.

Reference example 29

A solution of 2.50 g of 2-cyano-5-mercapto-1,3,4-thiadiazole in 50 ml of chloroform and 25 ml of ethanol was saturated with hydrogen chloride under ice-cooling. The mixture was stirred in a low temperature chamber (3°-5° C.) for 45 hours, and concentrated to dryness under reduced pressure. The residue was dissolved in 10 ml of methanol and 50 ml of ammonia-saturated methanol. The whole was stirred at 35°-37° C. for 48 hours, and distilled under reduced pressure to remove the solvent, and the residue was dissolved in ethyl acetate and diluted hydrochloric acid solution. The water layer was taken and concentrated under reduced pressure. The residue was washed with a (1:2) mixture of ethanol and ethyl acetate to give 1.30 g of 2-amidino-5-mercapto-1,3,4-thiadiazolehydrochloride as pale yellow crystals.

IR(KBr)cm$^{-1}$: 3300, 3220, 2970, 2720, 1670, 1640, 1490

NMR(d$_6$-DMSO)δ: 9.6–10.3(4H,br.)

MS m/e: 160(M)

Reference Example 30

7β-Amino-3-hydroxymethyl-3-cephem-4-carboxylic acid (1.38 g) and sodium hydrogen carbonate (1.51 g) were dissolved in 80 ml of a (1:1) mixture of water and THF, and 2.03 g of D(-)-α-(4-ethyl-2,3-dioxo-1-piperazinecarboxamido)phenylacetyl chloride was added under ice-cooling and stirring. The mixture was stirred under ice-cooling for an hour, adjusted to pH 6.5 and then concentrated under reduced pressure. The concentrate was subjected to a column chromatography on XAD-II (400 ml), being washed with water and eluted with 20% aqueous ethanol. The eluate was lyophilized to give 1.32 g of sodium 7β-[D-(-)-α-(4-ethyl-2,3-dioxo-1-piperazine carboxamido)-phenylacetamido]-3-hydroxymethyl-3-cephem -4-carboxylate as a pale yellow powder.

IR(KBr)cm$^{-1}$: 3280, 2970, 1760, 1710, 1670, 1600, 1510

NMR(d$_6$-DMSO)δ: 1.10(3H,t,J=6 Hz), 3.2–4.3(10H,m), 4.83(1H,d,J=5 Hz), 5.53(1H,dd,J=5&8 Hz), 5.66 (1H,d,J=7 Hz), 7.2–7.6(5H,m), 9.35(1H,d,J=8 Hz), 9.83(1H,d,J=7 Hz)

Elemental analysis for C$_{23}$H$_{24}$N$_5$NaO$_8$S.0.5H$_2$O:
Calcd.(%) : C,49.11; H,4.48; N,12.45.
Found(%) : C,49.16; H,4.75; N,12.23.

Reference Example 31

To a suspension of 7β-amino-3-hydroxymethyl-3-cephem-4-carboxylic acid (1.47 g) in 80 ml of a (1:1) mixture of water and THF was added 1.93 g of sodium hydrogen carbonate under ice-cooling and stirring.

To the mixture was added 2.56 g of 2-(5-chloro-2-chloroacetamidothiazol-4-yl)-(Z)-methoximinoacetyl-chloride hydrochloride, followed by stirring at room temperature for 30 minutes. Then, sodium N-methyldithiocarbamate (1.97 g) was gradually added to the mixture at room temperature under stirring to remove the protecting group for amino group (monitoring with TLC). To the reaction mixture were added water and ethyl acetate. The separated aqueous layer was adjusted to pH 6 and concentrated under reduced pressure. The concentrate was subjected to a column chromatography on XAD-II (200 ml) being eluted with water. The pertinent fractions containing the object compound were collected, concentrated to 30 ml and adjusted to pH 2.7. The resultant crystals were collected by filtration and washed with cold water to give 2.18 g of 7β-[2-(2-amino -5-chlorothiazol-4-yl)-(Z)-2-methyoxyiminoacetamido]-3 -hydroxymethyl-3-cephem-4-carboxylic acid as pale yellow crystals.

IR(KBr)cm$^{-1}$: 3320, 3220, 3060, 1760, 1680

NMR(d$_6$-DMSO)δ: 3.53(2H,br.s), 3.89(3H,s), 4.24(2H,s), 5.06(1H,d,J=5 Hz), 5.72(1H,dd,J=5&9 Hz), 7.31(2H,br.s), 9.48(1H,d,J=9 Hz)

Elemental analysis for C$_{14}$H$_{14}$ClN$_5$O$_6$S$_2$.0.5H$_2$O:
Calcd.(%) : C,36.80; H,3.31; N,15.33.
Found(%) : C,36.68; H,3.25; N,15,29.

Reference Example 32

To a suspension of 2-(2-tritylaminothiazol-4-yl) -(Z)-2-trityloxyiminoacetic acid (13.4 g) in 350 ml of acetonitrile were added 3.18 g of N-methylmorpholine and 8.38 g of 2,2'-dithiobisbenzothiazole under ice-cooling and stirring. To the mixture was added dropwise a solution of 6.27 g of triethyl phosphite in 60 ml of acetonitrile under ice-cooling and stirring, followed by stirring at the same temperature as above for 3 hours. The mixture was distilled to remove the solvent, and the residue was dissolved in a mixture of 400 ml of THF and 200 ml of dioxane.

On the other hand, 4.6 g of 7β-amino-3-hydroxymethyl -3-cephem-4-carboxylic acid was suspended in 200 ml of water and made a solution by addition of 1N-sodium hydroxide solution adjusting to pH 7. To this resulting solution was added the above solution, and the whole was stirred at room temperature for 95 hours. After removing the solvent, the residue was dissolved in 100 ml of THF and the solution was filtered to remove an insoluble material The filtrate was subjected to a column chromatography on silica gel (500 g) eluting with acetone/water (95:5). The eluate was evaporated to dryness under reduced pressure to give 10.0 g of sodium 3-hydroxymethyl-7β-[2-(2-tritylaminothiazol-4-yl)-(Z)-2-trityloxyiminoacetamido]-3-cephem-4-carboxylate as a pale yellow powder.

IR(KBr)cm$^{-1}$: 3380, 1770, 1690, 1590, 1520

NMR(d$_6$-DMSO)δ: 4.18(2H,ABq,J=13 Hz), 5.00(1H,d,J=5 Hz), 5.64(1H,dd,J=5&8 Hz), 6.59(1H,s), 7.00–7.45(30H,m)

Elemental analysis for C$_{51}$H$_{40}$N$_5$NaO$_6$S$_2$.5.5H$_2$O:
Calcd.(%) : C,60.94; H,5.11; N,6.97.
Found(%) : C,61.09; H,4.85; N,7.18.

Reference Example 33

Sodium 7β-[2-(5-chloro-2-tritylaminothiazol-4-yl) -(Z)-2-trityloxyiminoacetamido]-3-hydroxymethyl-3-cephem -4-carboxylate was obtained in a manner similar to that described in Reference Example 32.

IR(KBr)cm$^{-1}$:3430, 1765, 1675, 1600, 1535

NMR(d$_6$-DMSO)δ: 3.53(2H,ABq,J=18 Hz), 4.13(2H,ABq,J=12.6 Hz), 5.05(1H,d,J=4.8 Hz), 5.63(1H,dd,J=4.8&8.6 Hz), 7.15–7.50 (30H,m), 8.81(1H,s), 9.75(1H,d,J=8.6 Hz)

Reference Example 34

3-Amidinomethylthio-4-carbamoyl-5-mercaptoisothiazole was obtained in a manner similar to that described in Reference Example 14.

IR(KBr)cm$^{-1}$: 3250, 1640, 1550, 1360

NMR(CDCl$_3$)δ: 4.19(2H,s), 7.6–8.9 (5H,m)

Reference Example 35-37

The compounds shown in the following formula were obtained in a manner similar to that described in Reference Example 28. Their properties are shown in the following Table 1.

TABLE 1

HS—C(=N-N)-N(N=)-N((CH₂)ₙ—C(=NH)—NH₂)

| Reference Example No. | n | IR(KBr) cm⁻¹ | NMR(d₆-DMSO) |
|---|---|---|---|
| 35 | 2 | 3330, 3120, 1675, 1650 | 2.93(2H, t, J=7Hz), 4.50(2H, t, J=7Hz), 8.91(4H, br.) |
| 36 | 3 | 3250–3000, 1700, 1590, 1450 | 1.8–2.5(2H, m), 2.41 (2H, t, J=7Hz), 4.16 (2H, t, J=7Hz), 8.79 (3H, br.s) |
| 37 | 5 | 3250–3000, 1680, 1590, 1510, 1440 | 1.1–2.0(6H, m), 2.36 (2H, t, J=7Hz), 4.10 (2H, m), 8.4–9.1(3H, m) |

Example 1

7β-[2-(2-Aminothiazol-4-yl)-(Z)-2-methoxyiminoacetamido]-3-[[1-(2-guanidinoethyl)-1H-tetrazol-5-yl]thiomethyl]-3-cephem-4-carboxylic acid:

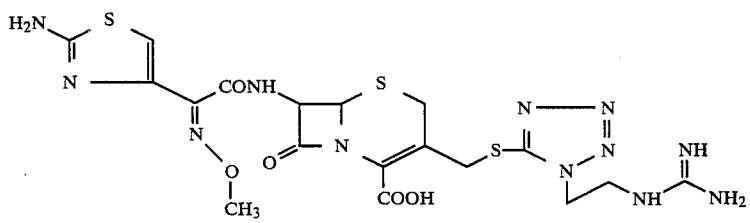

To a solution of 559 mg of tributylammonium 7β-[2-(2-aminothiazol-4-yl)-(Z)-2-methoxyiminoacetamido]-3-hydroxymethyl-3-cephem-4-carboxylate and 374 mg of 1-(2-guanidinoethyl)-5-mercapto-1H-tetrazole in 10 ml of DMF was added 500 mg of ethyl o-phenylenephosphate under stirring at −20° C. The reaction mixture was stirred at −20° C. to 0° C. for 90 minutes and subjected to a column chromatography on silica gel (100 g), being washed with acetonitrile and eluted with a (5:1) mixture of acetonitrile and water. The eluate was concentrated under reduced pressure, and the concentrate was subjected to a column chromatography on XAD-II (150 ml), being washed with water and eluted with 10% aqueous ethanol. The eluate was concentrated under reduced pressure and then lyophilized to give 245 mg of the title compound as a colorless powder.

IR(KBr)cm⁻¹: 1760, 1660, 1620, 1600, 1530
NMR(d₆-DMSO)δ: 3.2–3.8(4H,m), 3.84(3H,s), 4.22 (2H,ABq,J=13 Hz), 4.3–4.6(2H,m), 4.99(1H,d,J=5 Hz), 5.62(1H,dd,J=5&7.5 Hz), 6.75(1H,s), 7.18(2H,br.s), 7.7–7.9(5H,m), 9.54(1H,d,J=7.5 Hz)
Elemental analysis for $C_{18}H_{22}N_{12}O_5S_3 \cdot 1.5H_2O$:
Calcd.(%) : C,35.46; H,4.13; N,27.57.
Found(%) : C,35.43; H,3.81; N,27.43.

Example 2

7β-[2-(2-Aminothiazol-4-yl)-(Z)-2-ethoxyiminoacetamido]-3-[[1-(2-guanidinoethyl)-1H-tetrazol-5-yl]thiomethyl]-3-cephem-4-carboxylic acid:

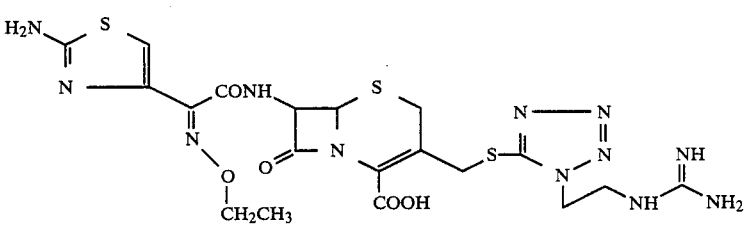

To a solution of 467 mg of sodium 7β-[2-(2-aminothiazol-4-yl)-(Z)-2-ethoxyiminoacetamido]-3-hydroxymethyl-3-cephem-4-carboxylate and 374 mg of 1-(2-guanidinoethyl)-5-mercapto-1H-tetrazole in 10 ml of DMF was added 500 mg of ethyl o-phenylenephosphate at −20° C. under stirring. The reaction mixture was stirred at −20° C. to 0° C. for 60 minutes, and was subjected to a column chromatography on silica gel (100 g), being washed with acetonitrile and eluted with a (5:1) mixture of acetonitrile and water. The eluate was concentrated under reduced pressure, and then subjected to a column chromatography on XAD-II (150 ml), being washed with water and eluted with 20% aqueous ethanol. The eluate was concentrated under reduced pressure and then lyophilized to give 333 mg of the title compound as a colorless powder.

IR(KBr)cm⁻¹: 1760, 1660, 1610, 1530
NMR(D₂O+DCl)δ: 1.52(3H,t,J=7 Hz), 3.7–4.2(4H,m), 4.53(2H,s), 4.55(2H,q,J=7 Hz), 4.85(2H,t,J=5 Hz), 5.44(1H,d,J=5 Hz), 5.96(1H,d,J=5 Hz), 7.36(1H,s)
Elemental analysis for $C_{19}H_{24}N_{12}O_5S_3 \cdot 2.3H_2O$:
Calcd.(%) : C,35.76; H, 4.52; N,26.34.
Found(%) : C,35.82; H,4.31; N,25.97.

Example 3

7β-[2-(2-Amino-5-chlorothiazol-4-yl)-(Z)-2-methoxyiminoacetamido]-3-[[1-(2-guanidinoethyl)-1H-tetrazol-5-yl]thiomethyl]-3-cephem-4-carboxylic acid:

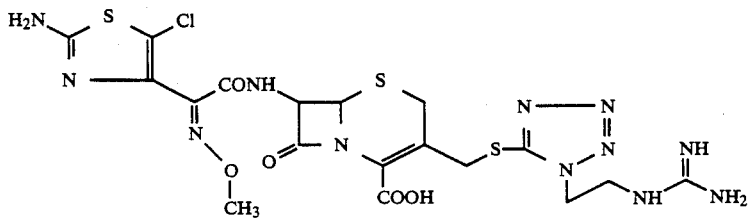

To a suspension of 457 mg of 7β-[2-(2-amino-5-chlorothiazol-4-yl-(Z)-2-methoxyiminoacetamido]-3-hydroxymethyl -3-cephem-4-carboxylic acid in 20 ml of water was added 10 ml of 0.1N sodium hydroxide solution under stirring and ice-cooling, followed by stirring under ice-cooling for 30 minutes. The mixture was lyophilized to give a powder. The resultant powder was allowed to react with 374 mg of 1-(2-guanidinoethyl)-5-mercapto -1H-tetrazole in the same manner as in Example 2 to give 391 mg of the title compound.

IR(KBr)cm$^{-1}$: 3180, 1760, 1660, 1620, 1535
NMR(d$_6$-DMSO)δ: 3.86(3H,s), 4.21(2H, ABq,J=13 Hz), 4.3–4.6(2H,m), 4.95(1H,d,J=5 Hz), 5.60(1H,dd,J=5&9 Hz), 7.31(2H,br.s), 7.67(2H,br.), 9.07(2H,br.), 9.46 (1H,d,J=9 Hz)

Elemental analysis for C$_{18}$H$_{21}$ClN$_{12}$O$_5$S$_3$.1.6H$_2$O:
Calcd.(%) : C,33.49; H,3.87; N,26.02.
Found(%) : C,33.36; H,3.45; N,25.69.

Example 4

3-[(2-Amidinomethylthio-1,3,4-thiadiazol-5-yl)thiomethyl]-7β-[2-(2-aminothiazol-4-yl)-(Z)-2-methoxyiminoacetamido]-3-cephem-4-carboxylic acid:

The title compound as a colorless powder was obtained in a manner similar to that described in Example 1.

IR(KBr)cm$^{-1}$: 1765, 1690(sh), 1670, 1600
NMR(D$_2$O+DCl)δ: 3.94(2H,ABq,J=17 Hz), 4.27(3H,s), 4.4–4.7(4H,s), 5.44(1H,d,J=5 Hz), 5.94(1H,d,J=5 Hz), 7.38 (1H,s)

Example 5

3-[(2-Amidinomethylthio-1,3,4-thiadiazol-5-yl)thiomethyl]-7β-[2-(2-aminothiazol-4-yl)-(Z)-2-ethoxyiminoacetamido]-3-cephem-4-carboxylic acid:

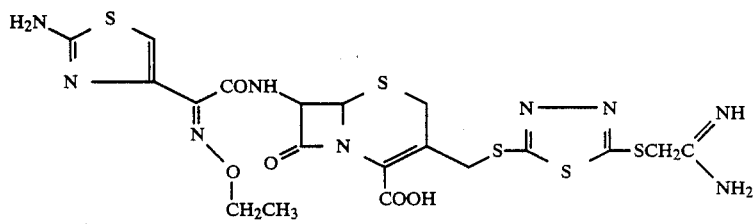

The title compound was obtained as a colorless powder in a manner similar to that described in Example 2.

IR(KBr)cm$^{-1}$: 1760, 1670(sh), 1650, 1600, 1525
NMR(D$_2$O+DCl)δ: 1.51(3H,t,J=7 Hz), 3.95(2H,ABq,J=17 Hz), 4.4–4.7(6H,m), 5.46(1H,d,J=5 Hz), 5.96(1H,d,J=5 Hz), 7.37(1 H,s)

Elemental analysis for C$_{19}$H$_{21}$N$_9$O$_5$S$_5$.2.2H$_2$O:
Calcd (%) : C,34.82; H,3.91; N,19.25.
Found(%) : C,34.92; H,3.57; N,18.89.

Example 6

3-[(2-Amidinomethylthio-1,3,4-thiadiazol-5-yl) thiomethyl]-7β-[2-(5-amino-1,2,4-thiadiazol-3-yl)-(Z) -2-methoxyiminoacetamido]-3-cephem-4-carboxylic acid:

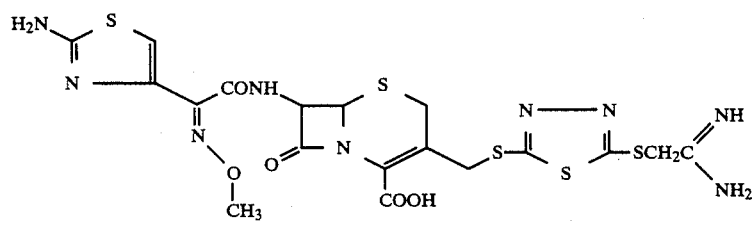

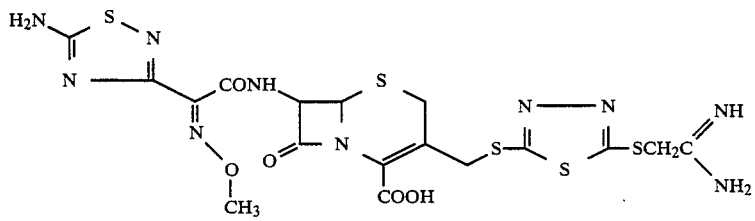

To a solution of 371 mg of sodium 7β-[2-(5-amino-1,2,4-thiadiazol-3-yl)-(Z)-2-methoxyiminoacetamido]-3-hydroxymethyl-3-cephem-4-carboxylate and 309 mg of 2-amidinomethylthio-5-mercapto-1,3,4-thiadiazole in 10 ml of DMF was added 600 mg of ethyl o-phenylenephosphate under stirring at −20° C. After stirring at −20° C. to 0° C. for 60 minutes, the mixture was subjected to a column chromatography on silica gel (100 g), being washed with acetonitrile and eluted with acetonitrile/water (4:1). The eluate was concentrated under reduced pressure, and the resultant solid was dissolved in dilute hydrochloric acid. This aqueous solution was subjected to a column chromatography on XAD-II (150 ml), being washed with water and eluted with 30% aqueous ethanol. The eluate was concentrated under reduced pressure and lyophilized to give 381 mg of the title compound as a colorless powder.

IR(KBr)cm$^{-1}$: 1760, 1675, 1620, 1590, 1520

NMR(D$_2$O+DCl+CD$_3$CN)δ: 3.93(2H,ABq,J=18 Hz), 4.34 (3H,s), 4.52(2H,s), 4.53(2H,br.s), 5.43(1H,d,J=4.5 Hz) 6.01(1H,d,J=4.5 Hz)

Example 7

3-[[1-(2-Amidinoethyl)-1H-tetrazol-5-yl]thiomethyl]-7β-[2-(2-aminothiazol-4-yl)-(Z)-2-methoxyiminoacetamido]-3-cephem-4-carboxylic acid:

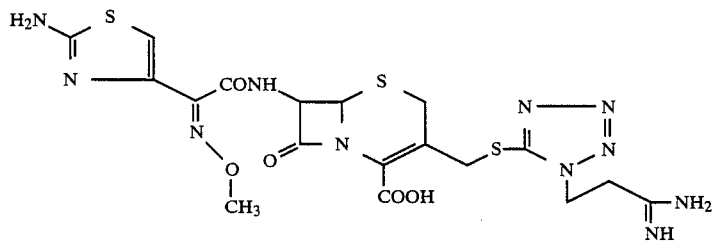

The title compound as a colorless powder was obtained in a manner similar to that described in Example 1.

IR(KBr)cm$^{-1}$: 1760, 1665, 1595, 1530

NMR(D$_2$O+DCl)δ: 3.37(2H,t,J=6 Hz), 4.0(2H,ABq,J=18 Hz), 4.03(3H,s), 4.51(2H,br.s), 5.46(1H,d,J=5 Hz), 5.97 (1H,d,J=5 Hz), 7.40(1H,s)

Elemental analysis for C$_{18}$H$_{22}$N$_{11}$O$_5$S$_3$.2.1H$_2$O:
Calcd.(%) : C,35.71; H,4.20; N,25.45.
Found(%) : C,35.93; H,4.07; N,25.17.

Example 8

7β-[2-(2-Aminothiazol-4-yl)-(Z)-2-methoxyiminoacetamido]-3-[[1-(3-guanidinopropyl)-1H-tetrazol-5-yl] thiomethyl]-3-cephem-4-carboxylic acid:

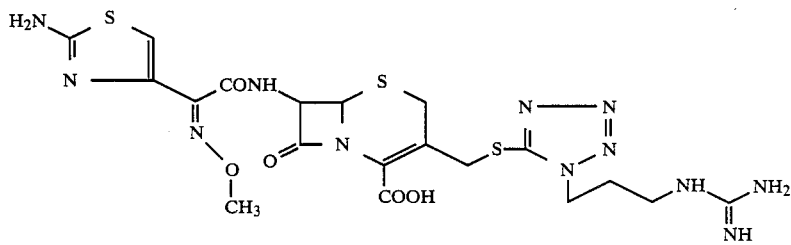

To a solution of 363 mg of sodium 7β-[2-(2-aminothiazol-4-yl)-(Z)-2-methoxyiminoacetamido]-3-hydroxymethyl-3-cephem-4-carboxylate and 241 mg of 1-(3-guanidinopropyl)-5-mercapto-1H-tetrazole in 10 ml of DMF was added 800 mg of ethyl o-phenylenephosphate under stirring at −20° C. The reaction mixture was stirred at −20° C. to 0° C. for 60 minutes and subjected to a column chromatography on silica gel (100 g), being washed with acetonitrile and eluted with acetonitrile/water (4:1). The eluate was concentrated under reduced pressure and subjected to a column chromatography on XAD-II (150 ml), being washed with water and eluted with 20% aqueous ethanol. The eluate was concentrated under reduced pressure and then lyophilized to give 294 mg of the title compound as a colorless powder.

IR(KBr)cm$^{-1}$: 1760, 1680, 1660, 1620, 1530

NMR(D$_2$O+DCl)δ: 2.43(2H,quintet,J=7 Hz), 3.98(2H,ABq, J=18 Hz), 4.29(3H,s), 4.55(2H,br.s), 4.73(2H,t,J=7 Hz), 5.45(1H,d,J=5 Hz), 5.97(1H,d,J=5 Hz), 7.40(1H,s)

Example 9

3-[(3-Amidinomethylthio-1,2,4-thiadiazol-5-yl) thiomethyl]-7β-[2-(2-aminothiazol-4-yl)-(Z)-2-methoxyiminoacetamido]-3-cephem-4-carboxylic acid:

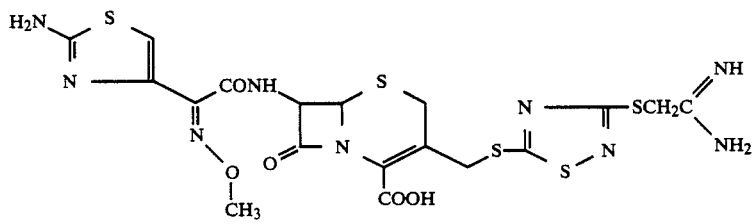

The title compound was obtained as a colorless powder in a manner similar to that described in Example 8.
IR(KBr)cm$^{-1}$: 1760, 1670, 1590, 1595
NMR(D$_2$O+DCl+CD$_3$CN)δ: 3.92(2H,ABq,J=18 Hz), 4.28(3H,s), 4.50(2H,s), 4.72(2H,ABq,J=13 Hz), 5.42(1H,d,J=5 Hz), 5.97(1H,d,J=5 Hz), 7.33(1H,s)

Example 10

3-[(6-Amidinomethylthio-3-pyridazinyl)thiomethyl]-7β-[2-(2-aminothiazol-4-yl)-(Z)-2-methoxyiminoacetamido]-3-cephem-4-carboxylic acid:

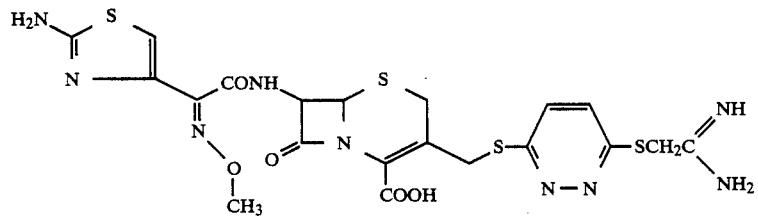

The title compound was obtained as an orange powder in a manner similar to that described in Example 8.
IR(KBr)cm$^{-1}$: 1760, 1690(sh), 1660, 1590, 1525
NMR(D$_2$O+CD$_3$CN)δ: 3.62(2H,ABq,J=18 Hz), 4.02(3H,s), 5.17(1H,d,J=5 Hz), 5.79(1H,d,J=5 Hz), 6.99(1H,s), 7.58(2H,s)

Example 11

7β-[2-(2-Aminothiazol-4-yl)-(Z)-2-methoxyiminoacetamido]-3-[[2-(2-guanidinoethylthio)-1,3,4-thiadiazol -5-yl]thiomethyl]-3-cephem-4-carboxylic acid:

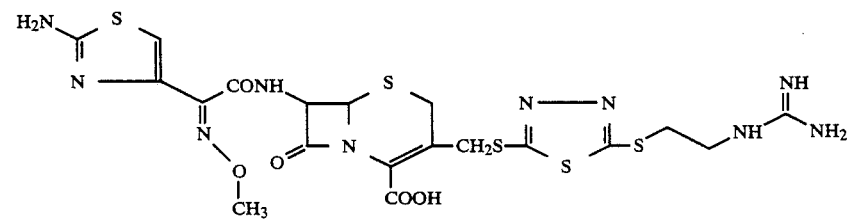

The title compound was obtained as a colorless powder in a manner similar to that described in Example 8.
IR(KBr)cm$^{-1}$: 1760, 1660, 1610, 1520
NMR(d$_6$-DMSO)δ: 3.1–3.8(6H,m), 3.84(3H,s), 4.87(2H, ABq,J=12 Hz), 5.03(1H,d,J=5 Hz), 5.62(1H,d,J=5 Hz), 6.73(1H,s), 7.16(2H,br.s), 7.58(2H,br.), 9.45(2H,br.)
Elemental analysis for C$_{19}$H$_{22}$N$_{10}$O$_5$S$_5$.0.5H$_2$O:
Calcd.(%) : C,35.67; H,3.62; N,21.89.
Found(%) : C,35.46; H,3.55; N,21.73.

Example 12

7β-[2-(2-Aminothiazol-4-yl)-(Z)-2-methoxyiminoacetamido]-3-[[2-(N,N-dimethylamidinomethylthio)-1,3,4-thiadiazol-5-yl]thiomethyl]-3-cephem-4-carboxylic acid:

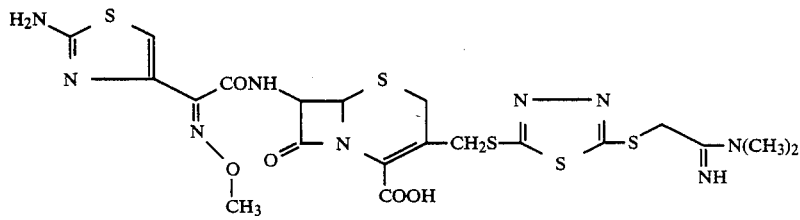

The title compound was obtained as a colorless powder in a manner similar to that described in Example 8.
IR(KBr)cm$^{-1}$: 1760, 1660, 1590, 1530, 1380
NMR(D$_2$O+CD$_3$CN)δ: 3.33(3H,s), 3.47(3H,s), 3.75(2H,ABq, J=18 Hz), 4.12(3H,s), 4.46(2H,s), 5.31(1H,d,J=6 Hz), 5.89(1H,d,J=6 Hz), 7.11(1H,s)
Elemental analysis for C$_{20}$H$_{23}$N$_9$O$_5$S$_5$.2H$_2$O:
Calcd.(%) : C,36.08; H,4.09; N,18.93.
Found(%) : C,36.28; H,3.82; N,18.91.

Example 13

3-[(5-Amidino-2-pyridyl)thiomethyl]-7β-[2-(2-aminothiazol-4-yl)-(Z)-2-methoxyiminoacetamido]-3-cephem-4-carboxylic acid:

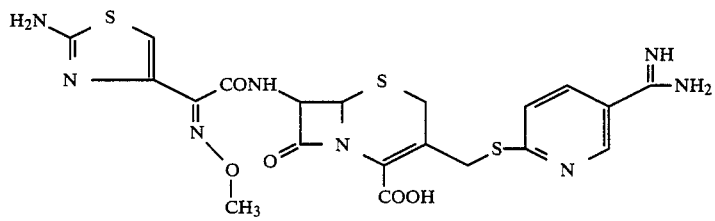

The title compound was obtained as a yellow powder in a manner similar to that described in Example 8.

IR(KBr)cm$^{-1}$: 1760, 1660, 1590, 1520

NMR(d$_6$-DMSO)δ: 3.86(3H,s), 5.01(1H,d,J=5 Hz), 5.5–5.7 (1H,m), 6.71(1H,s), 7.15(2H,br.), 7.4–9.0(3H,m)

Example 14

7β-[2-(2-Aminothiazol-4-yl)-(Z)-2-methoxyiminoacetamido]-3-[[2-(2-imidazolin-2-yl)methylthio-1,3,4-thiadiazol-5-yl]thiomethyl]-3-cephem-4-carboxylic acid:

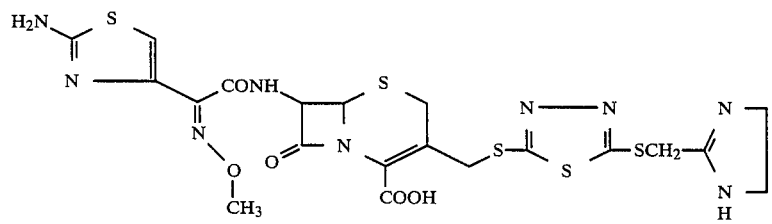

The title compound was obtained as a pale yellow powder in a manner similar to that described in Example 8.

IR(KBr)cm$^{-1}$: 3170, 2930, 1760, 1660, 1600

NMR(D$_2$O+DCl+CD$_3$CN)δ: 3.91(2H,ABq,J=18 Hz), 4.15(4H,s), 4.28(3H,s), 4.54(2H,ABq,J=13 Hz), 4.57(2H,s), 5.45 (1H,d,J=4.5 Hz), 5.95(1H,d,J=4.5 Hz), 7.37(1H,s)

Example 15

3-[(3-Amidinomethylthio-4-cyanoisothiazol-5-yl)thiomethyl]-7β-[2-(2-aminothiazol-4-yl)-(Z)-2-methoxyiminoacetamido]-3-cephem-4-carboxylic acid:

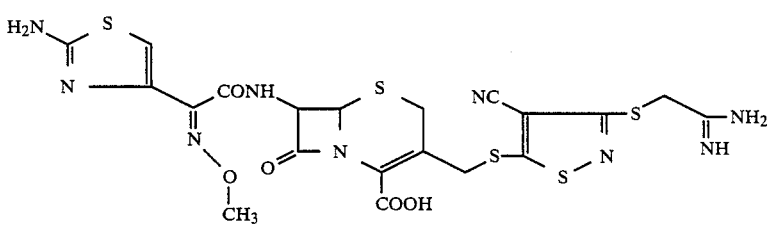

The title compound was obtained as a pale yellow powder in a manner similar to that described in Example 8.

IR(KBr)cm$^{-1}$: 2220, 1760, 1670, 1600, 1520

NMR(d$_6$-DMSO)δ: 3.50(2H,ABq,J=18 Hz), 3.83(3H,s), 4.23 (2H,br.s), 4.55(2H,ABq,J=13 Hz), 5.05(1H,d,J=5 Hz), 5.66(1H,dd,J=5&8 Hz), 6.73(1H,s), 7.16(2H,br.), 8.85 (2H,br.), 9.56(1H,d,J=18 Hz), 11.13(1H,br.)

Example 16

3-[(3-Amidinomethylthio-4-methyl-4H-1,2,4-triazol-5-yl)thiomethyl]-7β-[2-(2-aminothiazol-4-yl)-(Z)-2-methoxyiminoacetamido]-3-cephem-4-carboxylic acid:

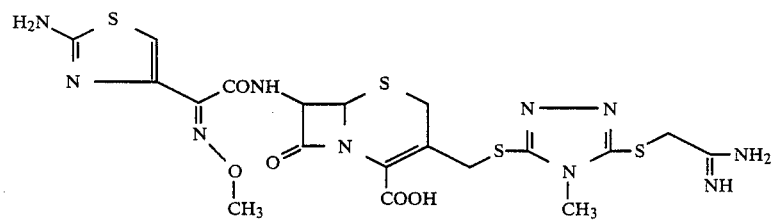

The title compound was obtained as a colorless powder in a manner similar to that described in Example 8.

IR(KBr)cm$^{-1}$: 1760, 1670, 1600, 1530, 1460

NMR(D₂O+DCl)δ: 4.02(3H,s), 4.06(2H,br.s), 4.32(3H,s), 4.46(2H,ABq,J=12 Hz), 4.51(2H,s), 5.55(1H,d,J=5 Hz), 5.99(1H,d,J=5 Hz), 7.41(1H,s)

Example 17

7β-[2-(2-Aminothiazol-4-yl)-(Z)-2-ethoxyiminoacetamido]-3-[[1-(3-guanidinopropyl)-1H-tetrazol-5-yl]thiomethyl]-3-cephem-4-carboxylic acid:

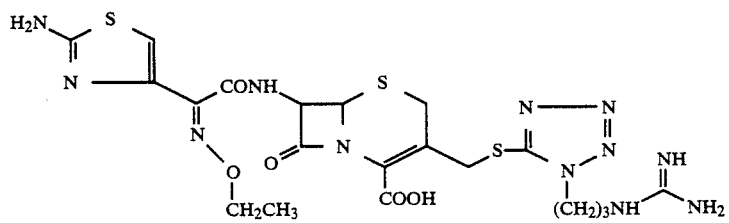

The title compound was obtained as a colorless powder in a manner similar to that described in Example 2.
IR(KBr)cm⁻¹: 1760, 1660, 1620, 1530, 1390

NMR(D₂O+DCl)δ: 1.53(3H,t,J=7 Hz), 2.2–2.6(2H,m), 3.46 (2H,t,J=6 Hz), 3.98(2H,ABq,J=18 Hz), 4.4–4.8(6H,m), 5.43(1H,d,J=5 Hz), 5.96(1H,d,J=6 Hz), 7.36(1H,s)
Elemental analysis for C₂₀H₂₀N₁₂O₅S₃·2.3H₂O:
Calcd.(%) : C,36.83; H,4.73; N,25.78.
Found(%) : C,37.22; H,4.54; N,25.38.

Example 18

7β-[2-(2-Aminothiazol-4-yl)-(Z)-2-methoxyiminoacetamido]-3-[[1-(4-guanidinobutyl)-1H-tetrazol-5-yl]thiomethyl]-3-cephem-4-carboxylic acid:

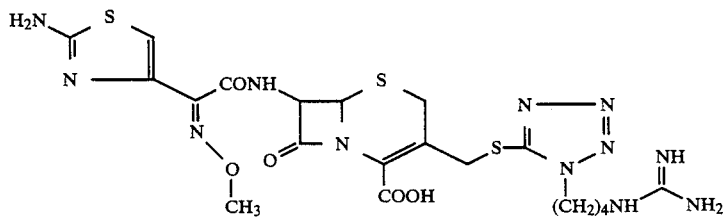

The title compound was obtained as a colorless powder in a manner similar to that described in Example 8.

IR(KBr)cm⁻¹: 1760, 1660, 1620, 1530
NMR(D₂O+DCl)δ: 1.65–2.30(4H,m), 3.42(2H,t,J=6 Hz), 3.97(2H,ABq,J=18 Hz), 4.28(3H,s), 4.52(2H,br.s), 4.67(2H,t,J=6 Hz), 5.43(1H,d,J=5 Hz), 5.96(1H,d,J=5 Hz), 7.38(1H,s)

Example 19

7β-[2-(2-Aminothiazol-4-yl)-(Z)-2-methoxyiminoacetamido]-3-[[4-cyano-3-(N-methylamidinomethylthio)isothiazol-5-yl]thiomethyl]-3-cephem-4-carboxylic acid:

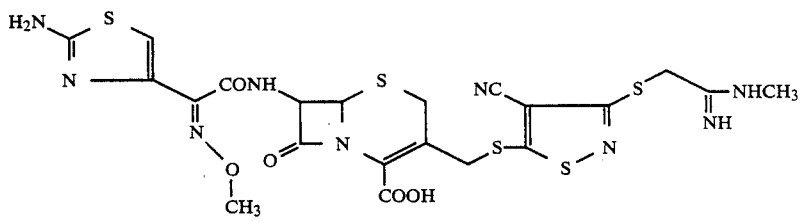

The title compound was obtained as an orange powder in a manner similar to that described in Example 8.
IR(KBr)cm⁻¹: 2230, 1770, 1680, 1600, 1530
NMR(d₆-DMSO)δ: 2.83(3H,s), 3.83(3H,s), 4.09(2H,br.s), 4.42(2H,ABq,J=14 Hz), 5.05(1H,d,J=5 Hz), 5.60(1H,dd,J=5&8 Hz), 6.73(1H,s), 7.15(2H,br.s), 9.53(1H,d,J=8 Hz)

Example 20

3-[(4-Amidinomethylthiothiazol-2-yl)thiomethyl]-7β-[2-(2-aminothiazol-4-yl)-(Z)-2-methoxyiminoacetamido]-3-cephem-4-carboxylic acid:

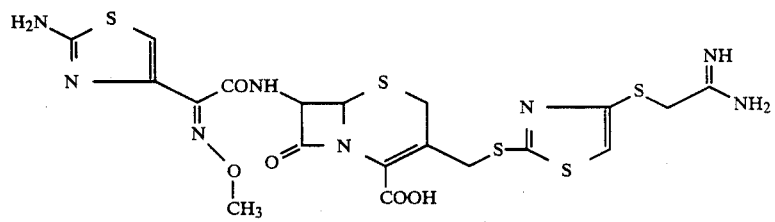

The title compound was obtained as a pale yellow powder in a manner similar to that described in Example 8.

IR(KBr)cm$^{-1}$: 1760, 1660, 1590, 1520, 1380
NMR(D$_2$O+DCl)δ: 3.93(2H,ABq,J=18 Hz), 4.17(2H,s), 4.29 (3H,s), 4.52(2H,ABq,J=14 Hz), 5.41(1H,d,J=5 Hz), 5.92 (1H,d,J=5 Hz), 7.39(1H,s), 7.97(1H,s)

Elemental analysis for C$_{19}$H$_{20}$N$_8$O$_5$S$_5$.1.9H$_2$O:
Calcd.(%) : C,35.94; H,3.78; N,17.65.
Found(%) : C,35.68; H,3.40; N,17.46.

Example 21

3-[(4-Amidinomethylthio-6-pyrimidinyl)thiomethyl]-7β-[2-(2-aminothiazol-4-yl)-(Z)-2-methoxyiminoacetamido]-3-cephem-4-carboxylic acid:

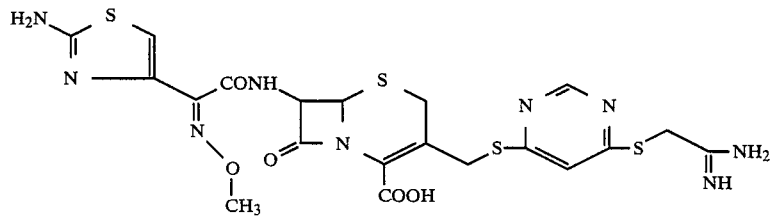

The title compound was obtained as an orange powder in a manner similar to that described in Example 8.
IR(KBr)cm$^{-1}$: 1760, 1660, 1600, 1530
NMR(d$_6$-DMSO)δ: 3.83(3H,s), 4.52(2H,br.s), 4.47(2H,ABq, J=13 Hz), 5.01(1H,d,J=5 Hz), 5.5–5.75(1H,m), 6.73(2H,s), 7.16(2H,br.s), 7.62(1H,s), 8.66(1H,s), 8.9–10.0(4H,m)

Elemental analysis for C$_{20}$H$_{21}$N$_9$O$_5$S$_4$.3H$_2$O:
Calcd.(%) : C,36.97; H,4.19; N,19.40.
Found(%) : C,36.91; H,3.82; N,19.13.

Example 22

3-[(3-Amidinomethylthio-4-amino-4H-1,2,4-triazol-5-yl)thiomethyl]-7β-[2-(2-aminothiazol-4-yl)-(Z)-2-methoxyiminoacetamido]-3-cephem-4-carboxylic acid:

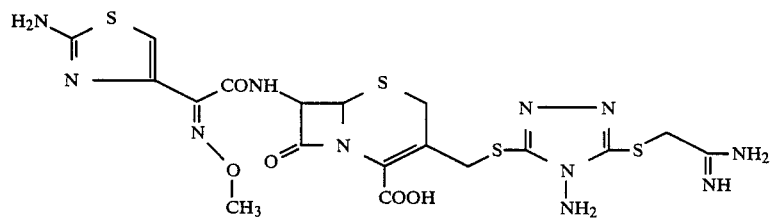

The title compound as a colorless powder was obtained in a manner similar to that described in Example 8.

IR(KBr)cm$^{-1}$: 1760, 1670, 1610, 1530
NMR(D$_2$O+DCl)δ: 4.03(2H,br.s), 4.32(3H,s), 4.43(2H,ABq, J=13 Hz), 4.49(2H,s), 5.49(1H,d,J=5 Hz), 5.97(1H,d,J=5 Hz), 7.39(1H,s)

Example 23

3-[[2-[N-(2-Amidinoethyl)carbamoyl]-1,3,4-thiadiazol-5-yl]thiomethyl]-7β-[2-(2-aminothiazol-4-yl)-(Z)-2-methoxyiminoacetamido]-3-cephem-4-carboxylic acid:

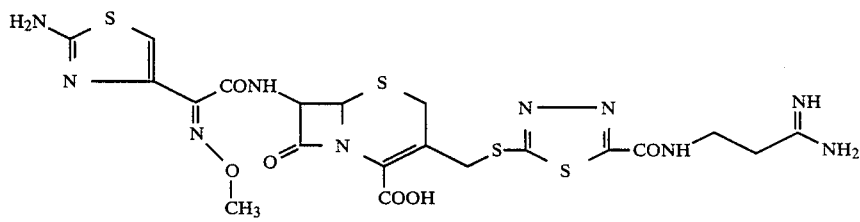

The title compound was obtained as a pale yellow powder in a manner similar to Example 8.
IR(KBr)cm$^{-1}$: 1760, 1660, 1600, 1520, 1380
NMR(D$_2$O+DCl)δ: 3.03(2H,t,J=6 Hz), 3.97(2H,ABq,J=18 Hz), 4.01(2H,t,J=6 Hz), 4.29(2H,s), 4.65(2H,ABq,J=14 Hz), 5.45(1H,d,J=5 Hz), 5.97(1H,d,J=5 Hz), 7.37(1H,s)

Elemental analysis for C$_{20}$H$_{22}$N$_{10}$O$_6$S$_4$.2.5H$_2$O:
Calcd.(%) : C,35.76; H,4.05; N,20.85.
Found(%) : C,35.48; H,3.81; N,20.51.

Example 24

3-[[3-[N-(2-Amidinoethyl)carbamoyl]-6-pyridyl]thiomethyl]-7β-[2-(2-aminothiazol-4-yl)-(Z)-2-methoxyimino acetamido]-3-cephem-4-carboxylic acid:

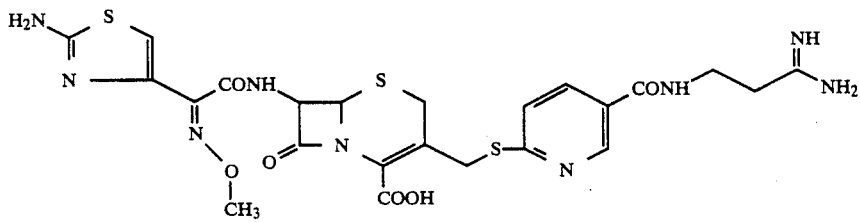

The title compound was obtained as a pale yellow powder in a manner similar to that described in Example 8.

IR(KBr)cm$^{-1}$: 1760, 1670, 1630, 1530, 1460
NMR(d$_6$-DMSO)δ: 2.55-2.85(2H,m), 3.81(3H,s), 4.31(2H,ABq, J=14 Hz), 4.98(1H,d,J=5 Hz), 5.58(1H,dd,J=5&8 Hz), 6.69 (1H,s), 7.13(2H,br.s), 7.2-9.0(3H,m), 9.0-9.9(6H,m)

Example 25

Sodium 7β-[2-(2-aminothiazol-4-yl)-(Z)-2-methoxyiminoacetamido]-3-[(3-cyanoamidinomethylthio-4-cyanoisothiazol-5-yl)thiomethyl]-3-cephem-4-carboxylate:

then lyophilized to give 187 mg of the title compound as a pink powder.

IR(KBr)cm$^{-1}$: 2180, 1765, 1640, 1570
NMR(d$_6$-DMSO)δ: 3.94(3H,s), 4.14(2H,br.s), 4.50(2H,ABq, J=12 Hz), 5.03(1H,d,J=5 Hz), 5.65(1H,dd,J=5&8 Hz), 6.72 (1H,s), 7.13(2H,br.s), 8.4-8.9(2H,m), 9.52(1H,d,J=8 Hz)

Elemental analysis for C$_{21}$H$_{17}$N$_{10}$NaO$_5$S$_5$.3.5H$_2$O:
Calcd.(%) : C,34.28; H,3.29; N,19.04
Found(%) : C,34.11; H,3.14; N,18.83

Example 26

Sodium 7β-[2-(2-aminothiazol-4-yl)-(Z)-2-methoxyiminoacetamido]-3-[(2-cyanoamidinomethylthio-1,3,4-

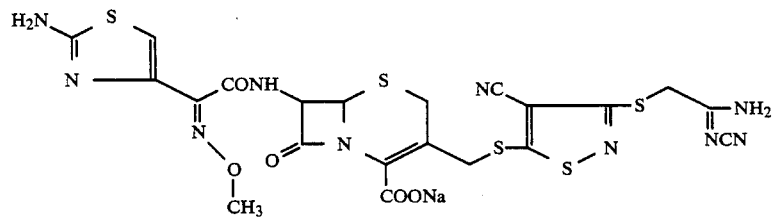

To a solution of sodium 7β-[2-(2-aminothiazol-4-yl)-(Z)-2-methoxyiminoacetamido]-3-hydroxymethyl-3-cephem -4-carboxylate (363 mg) and 3-cyanoamidinomethylthio-4-cyano-5-mercaptoisothiazole (410 mg) in 5 ml of acetonitrile and 5 ml of DMF was added 1.2 g of ethyl o-phenylenephosphate at −20° C. under stirring. After stirring at −20° C. to 5° C. for 2 hours, the reaction mixture was subjected to a column chromatography on silica gel (150 g), being washed with acetonitrile and eluted with acetonitrile/water (7:1). The eluate was concentrated under reduced pressure, adjusted to pH 7 and subjected to a column chromatography on XAD-II (150 ml), being washed with water and eluted with 30% aqueous ethanol. The eluate was concentrated under reduced pressure and thiadiazol-5-yl)thiomethyl]-3-cephem-4-carboxylate:

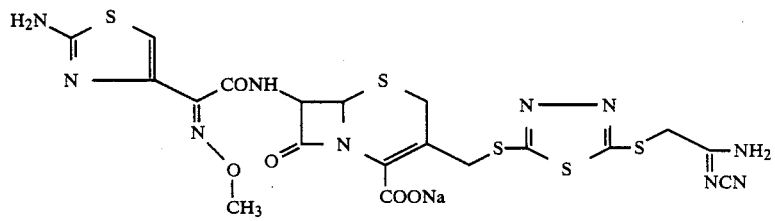

The title compound was obtained as a pale yellow powder in a manner similar to that described in Example 25.

IR(KBr)cm$^{-1}$: 2170, 1760, 1650, 1630, 1570
NMR(D$_2$O+CD$_3$CN)δ: 3.73(2H,ABq,J=18 Hz), 4.12(3H,s), 4.29 (2H,s), 4.42(2H,ABq,J=14 Hz), 5.28(1H,d,J=5 Hz), 5.89 (1H,d,J=5 Hz), 7.09(1H,s)

Example 27

Monosodium 3-[(3-amidinomethylthio-4-cyanoisothiazol-5-yl)thiomethyl]-7β -[2-(2-aminothiazol-4-yl)-(Z)-2-carboxymethoxyiminoacetamido]-3-cephem-4-carboxylate:

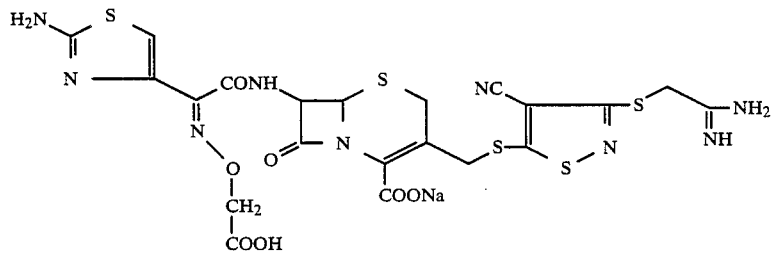

To a solution of sodium 7β-[2-(2-aminothiazol-4-yl)-(Z)-2-(tert-butoxycarbonylmethoxyimino)acetamido]-3-hydroxymethyl-3-cephem-4-carboxylate (554 mg) and 3-amidinomethylthio-4-cyano-5-mercaptoisothiazole (345 mg) in 7 ml of DMF was added 1.2 g of ethyl o-phenylenephosphate under stirring at −20° C. After stirring under ice-cooling for 2 hours, the reaction mixture was subjected to a column chromatography on silica gel (150 g), being washed with acetonitrile and eluted with acetonitrile/water (6:1). The eluate was concentrated. The resultant precipitate was collected by filtration and dissolved in 40 ml of trifluoroacetic acid under ice-cooling. The mixture was stirred at room temperature for an hour and distilled to remove the solvent. The residue was dissolved in a mixture of water and THF and then adjusted to pH 6 with an aqueous sodium hydrogencarbonate solution. The solution was washed with ethyl acetate, concentrated under reduced pressure and subjected to a column chromatography on XAD-II (150 ml), being washed with water and eluted with 20% aqueous ethanol. The eluate was concentrated under reduced pressure and lyophilized to give 363 mg of the title compound as a pale yellow powder.

IR(KBr)cm$^{-1}$: 2225, 1760, 1650(sh), 1590

NMR(D$_2$O)δ: 3.99(2H,ABq,J=18 Hz), 4.40(2H,ABq,J=13 Hz), 4.41(2H,br.s), 4.76(2H,br.s), 5.39(1H,d,J=5 Hz), 5.94 (1H,d,J=5 Hz), 7.13(1H,s)

Elemental analysis for C$_{21}$H$_{18}$N$_9$NaO$_7$S$_5$.5H$_2$O: Calcd.(%) : C,32.26; H,3.61; N,16.12. Found(%) : C,32.17; H,3.34; N,16.11.

Example 28

Monosodium 3-[(3-amidinomethylthio-4-cyanoisothiazol-5-yl)thiomethyl]-7β-[2-(2-aminothiazol-4-yl)-(Z)-2-(1-carboxy-1-methylethoxyimino)acetamido]-3-cephem-4-carboxylate:

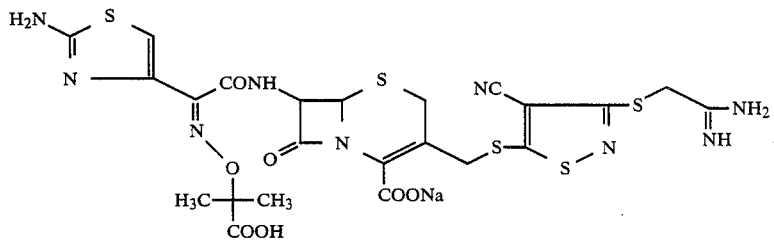

The title compound was obtained as a yellow powder in a manner similar to that described in Example 27.

IR(KBr)cm$^{-1}$: 2225, 1760, 1650(sh), 1580, 1520

NMR(d$_6$-DMSO)δ: 1.40(3H,s), 1.49(3H,s), 3.9–4.8(4H,m), 5.03(1H,d,J=5 Hz), 5.55–5.85(1H,m), 6.73(1H,s), 7.15 (2H,br.s)

Example 29

3-[[2-(2-Amidinopropylthio)-1,3,4-thiadiazol-5-yl]thiomethyl]-7β-[2-(2-aminothiazol-4-yl)-(Z)-2-methoxyiminoacetamido]-3-cephem-4-carboxylic acid:

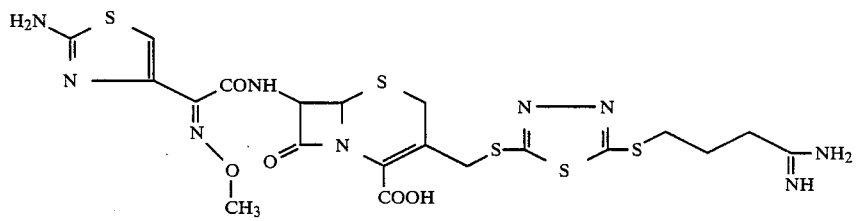

The title compound was obtained as a pale yellow powder in a manner similar to that described in Example 8.

IR(KBr)cm$^{-1}$: 1760, 1670, 1590, 1520, 1380

NMR(D$_2$O+DCl)δ: 2.15–2.55(2H,m), 2.87(2H,t,J=7 Hz), 3.53 (2H,t,J=7 Hz), 3.96(2H,ABq,J=18 Hz), 4.34(3H,s), 4.52 (2H,ABq,J=13 Hz), 5.45(1H,d,J=5 Hz), 5.94(1H,d,J=5 Hz), 7.38(1H,s)

Example 30

3-[[2-(2-Amidinoethylthio)-1,3,4-thiadiazol-5-yl]thiomethyl]-7β-[2-(2-aminothiazol-4-yl)-(Z)-2-methoxyiminoacetamido]-3-cephem-4-carboxylic acid:

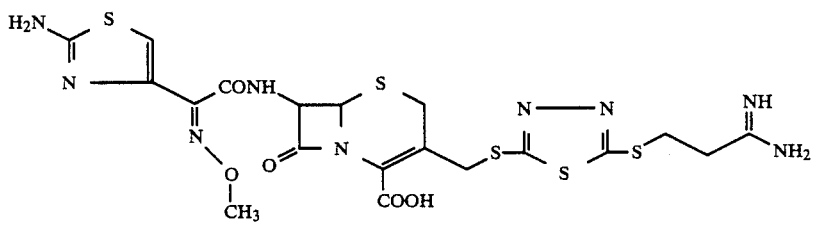

The title compound was obtained as a colorless powder in a manner similar to that described in Example 8.
IR(KBr)cm⁻¹: 1760, 1650, 1590, 1520, 1380
NMR(D₂O+DCl)δ: 3.23(2H,t,J=6 Hz), 3.93(2H,ABq,J=18 Hz), 4.26(3H,s), 4.53(2H,ABq,J=13 Hz), 5.45(1H,d,J=5 Hz), 5.93(1H,d,J=5 Hz), 7.34(1H,s)

Example 31

3-[[1-(2-Amidinomethylthioethyl)-1H-tetrazol-5-yl]thiomethyl]-7β-[2-(2-aminothiazol-4-yl)-(Z)-2-methoxy-iminoacetamido]-3-cephem-4-carboxylic acid:

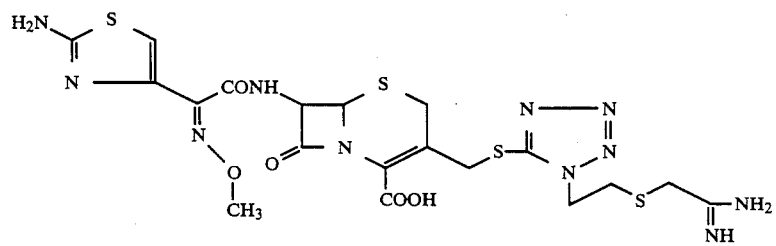

The title compound was obtained as a colorless powder in a manner similar to that described in Example 8.
IR(KBr)cm⁻¹: 1770, 1670, 1595, 1530, 1390
NMR(D₂O+DCl)δ: 3.42(2H,t,J=6 Hz), 3.86(2H,s), 3.97(2H, ABq,J=18 Hz), 4.32(3H,s), 4.55(2H,s), 4.92(2H,t, J=6 Hz), 5.44(1H,d,J=5 Hz), 5.95(1H,d,J=5 Hz), 7.40(1H,s)
Elemental analysis for C₁₉H₂₃N₁₁O₅S₄.2H₂O:
Calcd.(%) : C,35.11; H, 4.19; N,23.72. Found(%) : C,34.94; H,3.83; N,23.41.

Example 32

3-[[1-(2-Amidinomethylthioethyl)-1H-tetrazol-5-yl]thiomethyl]-7β-[2-(2-aminothiazol-4-yl)-(Z)-2-ethoxyiminoacetamido]-3-cephem-4-carboxylic acid:

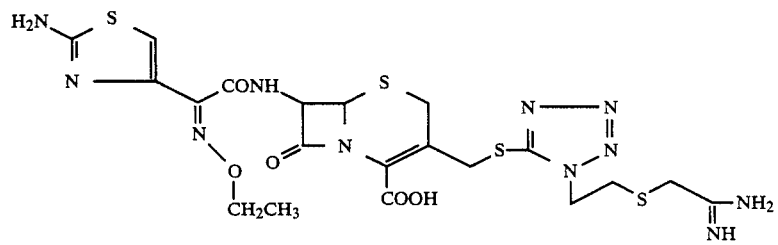

The title compound was obtained as a colorless powder in a manner similar to that described in Example 2.
IR(KBr)cm⁻¹: 1755, 1660, 1590, 1520, 1380
NMR(D₂O+DCl)δ: 1.53(3H,t,J=7 Hz), 3.42(2H,t,J=6 Hz), 3.81 (2H,s), 3.98(2H,ABq,J=18 Hz), 4.53(2H,s), 4.56(2H,q,J=7 Hz), 4.90(2H,t,J=6 Hz), 5.44(1H,d,J=5 Hz), 5.96(1H,d,J=5 Hz), 7.35(1H,s)
Elemental analysis for C₂₀H₂₅N₁₁O₅S₄.1 7H₂O:
Calcd.(%) : C,36.48, H,4.35, N,23.40. Found(%) : C,36.21; H,3.97; N,23.15.

Example 33

3-[[1-(2-Amidinomethylthioethyl)-1H-tetrazol-5-yl]thiomethyl]-7β-[2-(5-amino-1,2,4-thiadiazol-3-yl)-(Z)-2-methoxyiminoacetamido]-3-cephem-4-carboxylic acid:

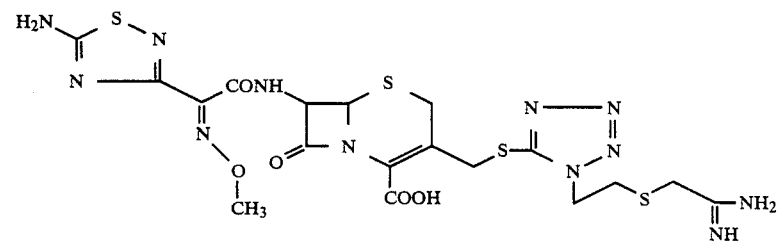

The title compound was obtained as a colorless powder in a manner similar to that described in Example 6.
IR(KBr)cm$^{-1}$: 1770, 1660, 1590, 1520, 1390
NMR(D$_2$O+DCl+CD$_3$CN)δ: 3.37(2H,t,J=6 Hz), 3.79(2H,s), 3.92 (2H,ABq,J=18 Hz), 4.28(3H,s), 4.52(2H,br.s), 4.83(2H,t, J=6 Hz), 5.38(1H,d,J=5 Hz), 6.00(1H,d,J=5 Hz)

Example 34

3-[[1-(2-Amidinomethylthioethyl)-1H-tetrazol-5-yl]thiomethyl]-7β-[2-(5-amino-1,2,4-thiadiazol-3-yl)-(Z)-2-ethoxyiminoacetamido]-3-cephem-4-carboxylic acid:

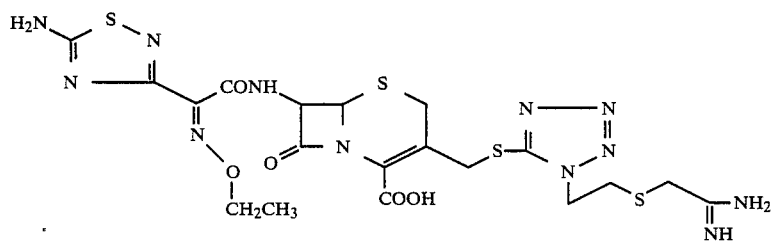

To a solution of sodium 7β-[2-(5-amino-1,2,4-thiadiazol-3-yl)-(Z)-2-ethoxyiminoacetamido]-3-hydroxymethyl-3-cephem-4-carboxylate (360 mg) and 1-(2-amidinomethylthioethyl)-5-mercapto-1H-tetrazole (262 mg) in 8 ml of DMF was added 1.0 g of ethyl o-phenylenephophate under stirring at −20° C. After stirring under ice-cooling for 1.5 hours, the reaction mixture was subjected to a column chromatography (silica gel, 100 g), being washed with acetonitrile and eluted with acetonitrile/water (4:1). The eluate was concentrated under reduced pressure and then subjected to a column chromatography (XAD-II, 150 ml), being washed with water and eluted with 20% aqueous ethanol. The eluate was concentrated under reduced pressure and lyophilized to give 159 mg of the title compound as a colorless powder.
IR(KBr)cm$^{-1}$: 1760, 1670, 1590, 1520
NMR(D$_2$O+DCl+DC$_3$CN)δ: 1.55(3H,t,J=7 Hz), 3.43(2H,t,J=6 Hz), 3.84(2H,s), 3.97(2H,ABq,J=18 Hz), 4.53(2H,s), 4.63(2H,q, J=7 Hz), 4.88(2H,t,J=6 Hz), 6.00(1H,d,J=5 Hz)

Example 35

3-[(2-Amidino-1,3,4-thiadiazol-5-yl)thiomethyl]-7β-[2-(2-aminothiazol-4-yl)-(Z)-2-methoxyiminoacetamido]-3-cephem-4-carboxylic acid:

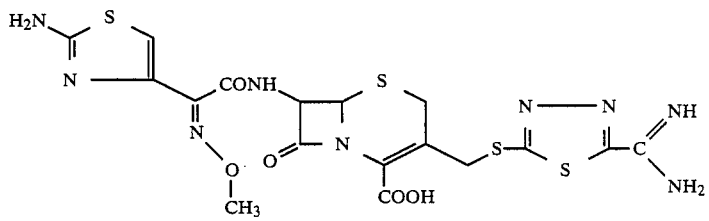

The title compound was obtained as pale yellow crystals in a manner similar to that described in Example 8.
IR(KBr)cm$^{-1}$: 1770, 1660, 1610, 1530, 1390
NMR(d$_6$-DMSO)δ: 3.72(2H,ABq,J=18 Hz), 3.94(3H,s), 4.53 (2H,ABq,J=13 Hz), 5.17(1H,d,J=5 Hz), 5.77(1H,d,J=5&8 Hz), 6.92(1H,s), 9.80(1H,d,J=8 Hz), 9.85(2H,br.s), 10.19(2H,br.s)

Example 36

3-[(2-Amidino-1,3,4-thiadiazol-5-yl)thiomethyl]-7β-[2-(2-aminothiazol-4-yl)-(Z)-2-ethoxyiminoacetamido]-3-cephem-4-carboxylic acid:

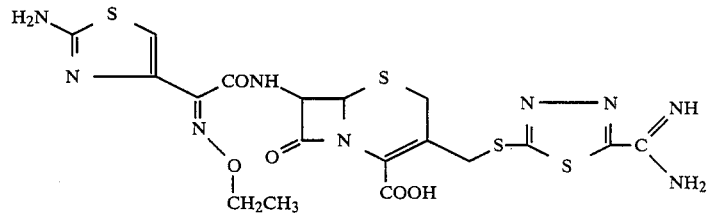

The title compound was obtained as pale yellow crystals in a manner similar to that described in Example 2.
IR(KBr)cm$^{-1}$: 2900, 1770, 1670, 1600, 1520
NMR(d$_6$-DMSO)δ: 1.23(3H,t,J=7 Hz), 3.60(2H,ABq,J=18 Hz), 4.10(2H,q,J=7 Hz), 4.60(2H,ABq,J=13 Hz), 5.08(1H,d,J=5 Hz), 5.6–5.8(1H,m), 6.69(1H,s), 7.16(2H,br.s), 9.50(1H,d,J=8 Hz)

Example 37

3-[2-Amidinomethylthio-1,3,4-thiadiazol-5-yl)thiomethyl]-7β-[D(−)-α-(4-ethyl-2,3-dioxo-1-piperazinecarboxamido)phenylacetamido]-3-cephem-4-carboxylic acid:

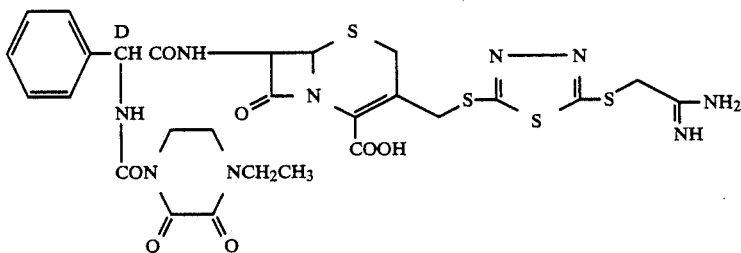

To a solution of 332 mg of sodium 7β-D(—)-α-(4-ethyl-2,3-dioxo-1-piperazinecarboxamido)-phenylacetamido]-3-hydroxymethyl-3-cephem-4-carboxylate and 106 mg of 2-amidinomethylthio-5-mercapto-1,3,4-thiadiazole in 8 ml of DMF was added 0.6 g of ethyl o-phenylenephosphate at −20° C. under stirring. The reaction mixture was stirred under ice-cooling for an hour and then subjected to a column chromatography on silica gel (100 g), being washed with acetonitrile and eluted with acetonitrile/water (5:1). The eluate was concentrated under reduced pressure and then subjected to a column chromatography on XAD-II (100 ml), being washed with water and eluted with 40% aqueous ethanol. The eluate was concentrated under reduced pressure. The resultant precipitate was collected by filtration to give 179 mg of the title compound as colorless crystals.

IR(KBr)cm$^{-1}$: 1765, 1700(sh), 1675, 1600
NMR(d$_6$-DMSO)δ: 1.08(3H,t,J=7 Hz), 3.8–4.3(5H,m), 4.68 (1H,d,J=13 Hz), 4.88(1H,d,J=6 Hz), 5.5–5.8(2H,m), 7.27.6(5H,m), 9.2–10.2(5H,m)
Elemental analysis for C$_{27}$H$_{29}$N$_9$O$_7$S$_4$.2H$_2$O: Calcd.(%) : C,42.90; H,4,40; N,16.68. Found(%) : C,42.95; H,4.18; N,16.38.

Example 38

3-[(4-Amidinomethylthio-6-pyrimidinyl)thiomethyl]-7β-[D(—)-α-(4-ethyl-2,3-dioxo-1-piperazinecarboxamido) phenylacetamido]-3-cephem-4-carboxylic acid:

NMR(d$_6$-DMSO+D$_2$O)δ: 1.08(3H,t), 3.75–4.2(5H,m), 4.58 (1H,d,J=13 Hz), 4.85(1H,d,J=5 Hz), 5.53(1H,d,J=5 Hz), 5.59(1H,s), 7.56(1H,s), 8.60(1H,s)

Example 39

3-[(2-Amidinomethylthio-1,3,4-thiadiazol-5-yl) thiomethyl]-7β-[2-(2-aminothiazol-4-yl)-(Z)-2-hydroxyiminoacetamido]-3-cephem-4-carboxylic acid:

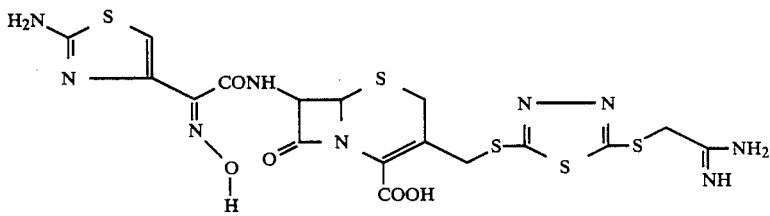

To a solution containing 906 mg of sodium 3-hydroxymethyl-7β-[2-(2-tritylaminothiazol-4-yl)-(Z)-2-trityloxyiminoacetamido]-3-cephem-4-carboxylate and 309 mg of 2-amidinomethylthio -5-mercapto-1,3,4-thiadiazole in 7 ml of DMF was added 1.01 g of ethyl o-phenylenephosphate under ice-cooling and stirring. The reaction mixture was stirred at room temperature for 4 hours and subjected to a column chromatography on silica gel (100 g), being washed with acetone and eluted with acetone/water (9:1). The eluate was concentrated to dryness under reduced pressure, and there was added 20 ml of formic acid. The mixture was stirred at room temperature for 16 hours and then distilled to remove formic acid. To the residue was added a mixture of water and THF. The solution was washed with ethyl acetate, concentrated under reduced pressure and then subjected to a column chromatography on XAD-II (140 ml), being washed with water and eluted with 20% aqueous ethanol. The eluate was concentrated to 10 ml and the resultant precipitate was collected by filtration

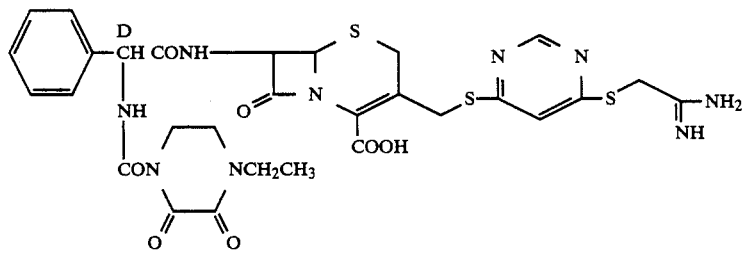

The title compound was obtained as a colorless powder in a manner similar to that described in Example 37.
IR(KBr)cm$^{-1}$: 1765, 1710(sh), 1675, 1600, 1530 to give 160 mg of the title compound as pale yellow crystals.
IR(KBr)cm$^{-1}$: 3275, 1755, 1660, 1595, 1520

NMR(d₆-DMSO)δ: 3.49(2H,ABq,J=18 Hz), 4.10(2H,s), 4.33 (2H,ABq,J=12 Hz), 5.00(1H,d,J=5 Hz), 5.65–5.80(1H,m), 6.65(1H,s), 7.07(2H,s)

Elemental analysis for $C_{17}H_{17}N_9O_5S_5 \cdot 1.5H_2O$:
Calcd.(%) : C,33.22; H,3.28; N,20.51. Found(%) : C,32.98; H,3.00; N,20.67.

Example 40

3-[(3-Amidinomethylthio-1,2,4-thiadiazol-5-yl) thiomethyl]-7β-[2-(2-aminothiazol-4-yl)-(Z)-2-hydroxyiminoacetamido]-3-cephem-4-carboxylic acid:

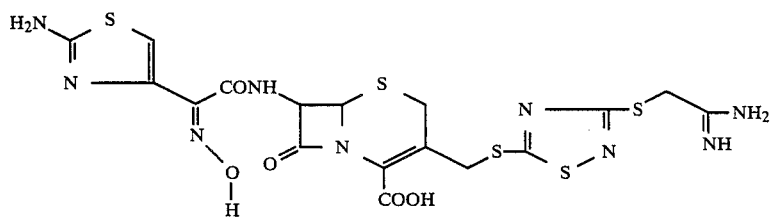

To a solution of 909 mg of sodium 3-hydroxymethyl-7β-[2-(2-tritylaminothiazol-4-yl)-(Z)-2-trityloxyiminoacetamido]-3-cephem-4-carboxylate and 619 mg of 3-amidino methylthio-5-mercapto-1,2,4-thiadiazole in 8 ml of DMF was added 1.4 g of ethyl o-phenylenephosphate under ice-cooling and stirring. The reaction mixture was stirred at room temperature for 4 hours and then subjected to a column chromatography on silica gel (150 g), being eluted with aceton/water (95:5). The eluate was concentrated to dryness under reduced pressure to obtain a powder to which was added 20 ml of formic acid. After stirring at room temperature for 14 hours, the mixture was distilled under reduced pressure to remove formic acid. The residue was added with water and THF, adjusted to pH 7 under ice-cooling, washed with ethyl acetate, concentrated under reduced pressure and then subjected to a column chromatography on XAD-II (140 mg), being washed with water and eluted with 20% aqueous ethanol. The eluate was concentrated under reduced pressure and then lyophilized to give 155 mg of the title compound as a pale yellow powder.

IR(KBr)cm⁻¹: 3280, 1760, 1680, 1590, 1520

NMR(d₆-DMSO)δ: 4.2–5.0(4H,m), 5.03(1H,d,J=5 Hz), 5.65 (1H,dd,J=5&8 Hz), 6.65(1H,s), 7.14(2H,br.s), 9.24–9.46 (2H,m), 9.44(1H,d,J=8 Hz), 10.42–10.48(2H,m), 11.29(1H,s)

Elemental analysis for $C_{17}H_{17}N_9O_5S_5 \cdot 2H_2O$:
Calcd.(%) : C,32.74; H,3.39; N,20.21.
Found(%) : C,32.69; H,3.07; N,19.89.

Example 41

3-[(4-Amidinomethylthiothiazol-2-yl)thiomethyl]-7β-[2-(2-aminothiazol-4-yl)-(Z)-2-hydroxyiminoacetamido]-3-cephem-4-carboxylic acid:

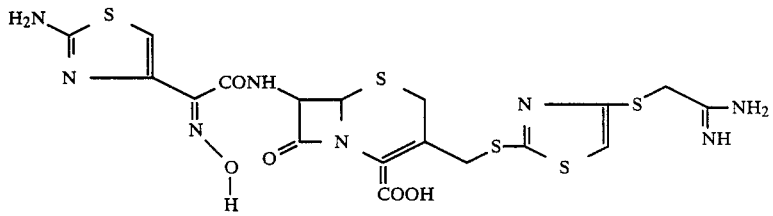

The title compound was obtained as a yellow powder in a manner similar to that described in Example 40.

IR(KBr)cm⁻¹: 1775, 1660(sh), 1590, 1510

NMR(d₆-DMSO)δ: 3.27(1H,d,J=18 Hz), 3.98(1H,s), 4.42(2H, ABq,J=12 Hz), 4.95(1H,d,J=5 Hz), 5.65(1H,dd,J=5&8 Hz), 6.63(1H,s), 7.05(2H,br.s), 7.60(1H,s), 9.32(1H,d, J=8 Hz), 9.36(2H,br.s), 9.72(2H,br.s)

Example 42

3-[(3-Amidinomethylthio-4-cyanoisothiazol-5-yl) thiomethyl]-7β-[2-(2-aminothiazol-4-yl)-(Z)-2-hydroxyiminoacetamido]-3-cephem-4-carboxylic acid:

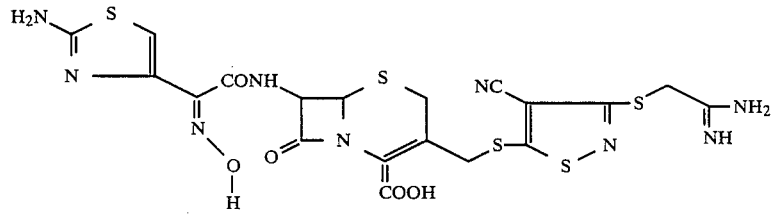

The title compound was obtained as yellow crystals in a manner similar to that described in Example 39.

IR(KBr)cm⁻¹: 2225, 1755, 1650, 1595, 1510

NMR(d₆-DMSO)δ: 4.23(2H,br.s), 4.56(2H,ABq,J=13 Hz), 5.05 (1H,d,J=5 Hz), 5.68(1H,dd,J=5&8 Hz), 6.62(1H,s), 7.05 (2H,br.s), 9.43(1H,d,J=8 Hz), 8.82(2H,br.s), 10.9–11.2 (3H,m)

Elemental analysis for $C_{19}H_{17}N_9O_5S_5 \cdot 2.5H_2O$:
Calcd.(%) : C,34.75; H,3.38; N,19.19. Found(%) : C,34.65; H,3.39; N,18.89.

Example 43-52

The following compounds were obtained in a manner similar to that described in Example 40, whose physical properties are shown in Table 2 and Table 3.

TABLE 2

General structure (Examples 43-47):

H₂N–C(S)–N=C(X)–... CONH–[β-lactam]–CH₂–S–R with =N–OH oxime and COOH

| Example No. | X | R | IR(KBr) cm⁻¹ |
|---|---|---|---|
| 43 | H | –C(CONH₂)=C(S–N)–S–CH₂–C(=NH)NH₂ (thiazole with CONH₂, S-CH₂-amidine) | 1755, 1655, 1610, 1580, 1540 |
| 44 | H | tetrazolyl–CH₂CH₂–S–CH₂–C(=NH)NH₂ | 1760, 1670, 1630, 1600, 1530 |
| 45 | H | pyrimidinyl–S–CH₂–C(=NH)NH₂ | 1750, 1680(sh), 1650, 1600, 1530 |
| 46 | H | tetrazolyl–CH₂CH₂–C(=NH)NH₂ | 1760, 1660, 1600, 1520 |
| 47 | H | tetrazolyl–N–(CH₂)₃–C(=NH)NH₂ | 1760, 1660, 1595, 1520, 1385, 1350 |

TABLE 2-continued

| Example No. | X | R | IR(KBr) cm⁻¹ |
|---|---|---|---|
| 48 | H | tetrazolyl–N–(CH₂)₅–C(=NH)NH₂ | 1760, 1670, 1600, 1520, 1380 |
| 49 | Cl | –C(CN)=C(S–N)–S–CH₂–C(=NH)NH₂ | 2220, 1765, 1665, 1535 |
| 50 | Cl | thiadiazolyl–S–CH₂–C(=NH)NH₂ | 1765, 1665, 1620, 1540 |
| 51 | Cl | tetrazolyl–N–CH₂CH₂–C(=NH)NH₂ | 1765, 1665, 1600, 1510 |
| 52 | H | tetrazolyl–N–CH₂CH₂–(cyclic amidine, imidazoline) | 1760, 1660(sh), 1600, 1525 |

TABLE 3

| Example No. | NMR, δ |
|---|---|
| 43 | (d₆-DMSO):3.62(1H,d,J = 18Hz), 4.13(2H,br.s), 4.34(2H,ABq,J = 13.2Hz), 5.03(1H,d,J = 4.9Hz), 5.65(1H,dd,J = 4.9 & 8.2Hz), 6.63 (1H,s), 7.13(2H,br.s), 8.75(2H,br.s), 9.44(1H,d,J = 8Hz), 11.30(1H,s) |
| 44 | (d₆-DMSO):3.21(2H,t,J = 6.4Hz), 4.08(1H,d,J = 11.6Hz), 4.45–4.70(3H,m), 5.00(1H,d,J = 4.7Hz), 5.66(1H,dd,J = 4.7 & 8.1Hz), 6.60(1H,s), 7.13(2H,br.s), 9.25–9.60(4H,m), 11.30(1H,s) |
| 45 | (d₆-DMSO):3.61(1H,d,J = 19.2Hz), 4.29(2H,br.s), 4.42(2H,ABq, J = 13.6Hz), 5.02(1H,d,J = 4.8Hz), 5.61(1H,d,J = 4.8 & 7.8Hz), 6.50 (1H,s), 7.15(2H,br.s), 7.62(1H,s), 8.65(1H,s), 9.0–9.6(2H,m) |
| 46 | (D₂O + DCl):3.16(2H,t,J = 6.2Hz), 3.80(2H,ABq,J = 18.8Hz), 4.29 (2H,ABq,J = 13.2Hz), 5.27(1H,d,J = 4.8Hz), 5.80(1H,d,J = 4.8Hz), 7.16(1H,s) |
| 47 | (D₂O + DCL):2.35(2H,quintet,J = 7Hz), 2.61(2H,t,J = 7Hz), 3.79 (2H,ABq,J = 18Hz), 4.28(2H,ABq,J = 13.8Hz), 4.55(2H,t,J = 7Hz), 5.26(1H,d,J = 5Hz), 5.78(1H,d,J = 5Hz), 7.15(1H,s) |
| 48 | (D₂O + DCl):1.37(2H,m), 1.73(2H,m), 1.95(2H,m), 2.49(2H,t,J = 7Hz), 3.78(2H,ABq,J = 18Hz), 4.30(2H,br.s), 4.46(2H,t,J = 7Hz), 5.25(1H,d,J = 4.8Hz), 5.78(1H,d,J = 4.8Hz), 7.17(1H,s) |
| 49 | (d₆-DMSO):3.62(1H,d,J = 18Hz), 4.25(2H,s), 4.55(2H,ABQ,J = 13Hz), 5.04(1H,d,J = 5Hz), 5.69(1H,dd,J = 5 & 8Hz), 7.33(2H,s), 9.43(1H,d,J = 8Hz), 11.70(1H,s) |
| 50 | (d₆-DMSO):3.64(1H,d,J = 17.8Hz), 4.09(2H,s), 4.36(2H,ABq,J = 21.6Hz), 4.99(1H,d,J = 5Hz), 5.73(1H,dd,J = 5 & 8Hz), 7.31(2H,s), |

TABLE 3-continued

| Example No. | NMR, δ |
|---|---|
| | 9.36(1H,d,J = 8Hz), 9.4–9.96(3H,m), 11.71(1H,s) |
| 51 | (D₂O + DCl):3.81(2H,t,J = 7Hz), 3.81(2H,ABq,J = 18.3Hz), 4.87(2H, t,J = 7Hz), 5.28(1H,d,J = 4.8Hz), 5.80(1H,d,J = 4.8Hz) |
| 52 | (D₂O + DCl):3.24(2H,t,J = 6.4Hz), 3.81(2H,ABq,J = 17.6Hz), 3.91 (4H,s), 4.31(2H,ABq,J = 13.4Hz), 5.28(1H,d,J = 4.7Hz), 5.80 (1H,d,J = 4.7Hz), 7.16(1H,s) |

Test Example 1

The following shows the Minimal Inhibitory Concentrations of representative compounds of this invention.

The Minimal Inhibitory Concentrations of the tested compounds were determined according to the agar dilution method. Namely, 1.0 ml each of aqueous solution of the test compounds diluted by serial dilutions was poured into test petri dishes, subsequently 9.0 ml each of Trypticase soy agar was poured into the dishes and mixed.

On each of the mixed agar plates, one loopful of bacterial suspension (about 10⁸ CFU/ml) of test microorganism was streaked.

After the incubation at 37° C. for 18 hours, the lowest concentration of the tested compounds in the medium which caused apparently complete inhibition of growth of the test microorganism was taken to be minimal inhibitory concentration. Antibacterial activity (minimal inhibitory concentration) of the test compounds are shown in the Table 4.

TABLE 4

| | MIC(μg/ml) | | | | |
|---|---|---|---|---|---|
| | Test Compound (Ex. No.) | | | | |
| Microorganism | 8 | 15 | 39 | 42 | 44 |
| S. aureus FDA 209P | 0.78 | 0.2 | 0.2 | ≦0.1 | ≦0.1 |
| S. aureus 308 A-1 | 0.78 | 0.2 | 0.2 | ≦0.1 | ≦0.1 |
| S. aureus 1840 | 0.78 | 0.39 | 0.39 | 0.2 | 0.2 |
| S. aureus N-241 | 12.5 | 6.25 | 1.56 | 0.78 | 3.13 |
| S. aureus J-108 | 6.25 | 6.25 | 1.56 | 0.78 | 3.13 |
| E. coli NIHJ JC-2 | ≦0.1 | 0.39 | 0.39 | 0.78 | 0.2 |
| E. coli O-111 | ≦0.1 | ≦0.1 | ≦0.1 | ≦0.1 | ≦0.1 |
| E. coli T 7 | 0.39 | 0.39 | 1.56 | 1.56 | 0.78 |
| C. freundii IFO12681 | ≦0.1 | 0.2 | 0.39 | 0.78 | 0.39 |
| K. pneumoniae DT | ≦0.1 | 0.2 | ≦0.1 | 0.78 | 0.2 |
| E. cloacae IFO12937 | 0.39 | 0.78 | 3.13 | 3.13 | 3.13 |
| S. marcescens IFO12648 | ≦0.1 | 0.39 | 0.78 | 1.56 | 0.39 |
| P. vulgaris IFO3988 | ≦0.1 | 0.2 | 0.78 | 0.78 | 0.39 |
| P. mirabilis IFO3849 | 0.39 | 0.78 | 1.56 | 3.13 | 3.13 |
| M. morganii IFO3168 | ≦0.1 | 0.2 | 0.39 | 0.78 | 0.39 |
| P. aeruginosa IFO3455 | 6.25 | 6.25 | 12.5 | 12.5 | 12.5 |

What is claimed is:

1. A compound of the formula

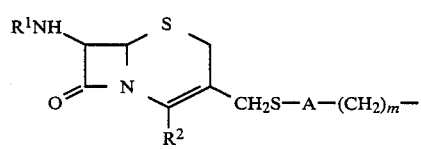

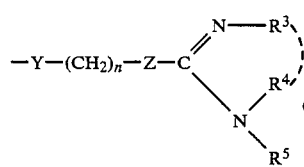

wherein $R^1$ is an acyl group of the formula

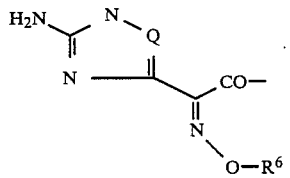

wherein Q is a nitrogen atom, CH or C—Cl, and $R^6$ is a hydrogen atom or a lower alkyl which is unsubstituted or substituted by carboxyl, a group of the formula

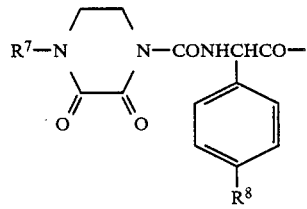

wherein $R^7$ is a lower alkyl group, and $R^8$ is a hydrogen atom or hydroxyl group, or a group of the formula

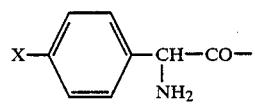

wherein

X is a hydrogen or halogen atom or a hydroxyl group, $R^2$ is an unsubstituted carboxy group or a carboxy group esterified with a group of the formula

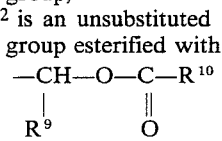

wherein $R^9$ is a hydrogen atom, a $C_{1-6}$ alkyl, $C_{3-7}$ cycloalkyl or $C_{3-7}$ cycloalkyl-$C_{1-6}$ alkyl group and $R^{10}$ is a hydrogen atom, a $C_{1-6}$ alkyl, $C_{3-7}$ cycloalkyl, $C_{1-10}$ alkoxy, $C_{3-7}$ cycloalkyloxy, $C_{3-7}$ cycloalkyl-$C_{1-6}$ alkyl, $C_{3-7}$ alkenyloxy, phenyl, phthalidyl, (2-oxo-5-methyl-1,3-dioxolen-4-yl)methyl, a $C_{1-10}$ alkoxy-$C_{1-6}$ alkyl, a $C_{1-6}$ alkylthio-$C_{1-6}$ alkyl, 2,2,2-trichloroethyl, benzyl, p-methoxybenzyl, p-nitrobenzyl, benzhydryl, trityl or trimethylsilyl group, $R^3$ is a hydrogen atom, a $C_{1-6}$ alkyl or a cyano group;

$R^4$ is a hydrogen atom or a $C_{1-6}$ alkyl group; or wherein $R^4$ together with $R^3$ is a methylene chain having two or three carbon atoms;

$R^5$ is a hydrogen or a $C_{1-6}$ alkyl group;

A is an unsubstituted or substituted bivalent aromatic heterocyclic group wherein the aromatic heterocycle is a five- or six- membered aromatic heterocycle containing 1 to 4 hetero atoms of nitrogen, oxygen and sulfur atoms and which is bonded on a ring-constituting carbon atom with the adjacent sulfur atom, the substituents being one to three members of the group consisting of cyano, amino, $C_{1-4}$ alkyl, halogen, carbamoyl and $C_{1-4}$ alkoxycarbonyl;

Y is a chemical bond, sulfur or oxygen atom, —NH—, CONH—, or —NHCO—;

Z is a chemical bond, or —NH—;

m is an integer of 0 to 4 and n is an integer of 0 to 6; or a pharmacologically acceptable salt thereof.

2. A composition of claim 1 in which the acyl group $R_1$ is a group of the formula:

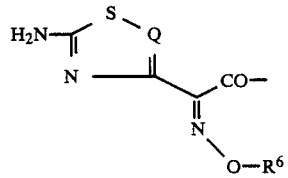

wherein Q is nitrogen atom, CH or C—Cl and $R^6$ is hydrogen atom or a lower alkyl group which may be substituted by carboxy.

3. A compound of claim 2 in which the lower alkyl group which may be substituted by carboxy is a methyl, ethyl, propyl or isopropyl group which may be substituted by carboxy.

4. A compound of claim 1 in which the acyl group $R^1$ is a group of the formula:

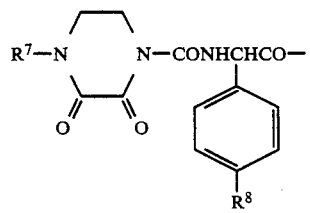

wherein $R^7$ is a lower alkyl group and $R^8$ is hydrogen atom or hydroxy group.

5. A compound of claim 4 in which the lower alkyl group is methyl, ethyl or propyl group.

6. A compound of claim 1 in which the acyl group $R^1$ is a group of the formula:

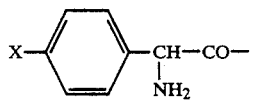

wherein X is hydrogen atom, a halogen atom or hydroxy group.

7. A compound of claim 1 in which the group A is a five- or six-membered aromatic heterocycle containing 1 to 4 nitrogen atoms or a five-membered aromatic heterocycle containing 1 to 2 nitrogen atoms and one sulfur atom.

8. A compound of claim 7 in which the five- or six-membered aromatic heterocycle containing 1 to 4 nitrogen atoms is tetrazole, triazole, pyridazine, pyrimidine or pyridine.

9. A compound of claim 7 in which the five-membered aromatic heterocycle containing 1 to 2 nitrogen atoms and one sulfur atom is 1,3,4-thiadiazole, 1,2,4-thiadiazole, thiazole or isothiazole.

10. A compound of claim 1 in which the moiety of

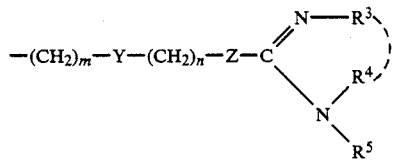

in the formula (I) is a moiety where m is zero, Y is a binding arm, and $R^3$, $R^4$ and $R^5$ are hydrogen.

11. A compound of claim 1 in which the moiety of

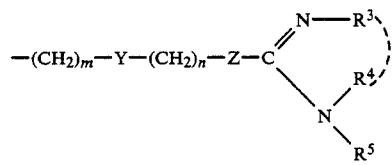

in the formula (I) is a moiety where m is zero, Y is sulfur or oxygen, $R^3$ is hydrogen, methyl or cyano, $R^4$ is hydrogen or methyl, and $R^5$ is hydrogen.

12. A compound of claim 1 in which the moiety of

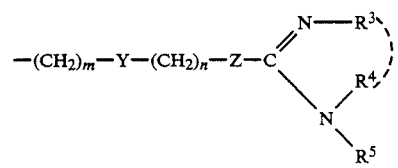

in the formula (I) is a moiety where Y is sulfur, Z is a binding arm, n is 1, $R^3$, $R^4$ and $R^5$ are hydrogen.

13. A compound of claim 1 which is
3-[(2-amidinomethylthio-1,3,4-thiazol-5-yl)thiomethyl]-7β-[2-(2-aminothiazol-4-yl)-(Z)-2-hydroxyiminoacetamido]-3-cephem-4-carboxylic acid,
3-[(3-amidinomethylthio-4-cyanoisothiazol-5-yl)thiomethyl]-7β-[2-(2-aminothiazol-4-yl)-(Z)-2-hydroxyiminoacetamido]-3-cephem-4-carboxylic acid,
3-[[1-(2-amidinoethylthioethyl)-1H-tetrazol-5-yl]thiomethyl]-7β-[2-(2-aminothiazol-4-yl)-(Z)-2-hydroxyiminoacetamido]-3-cephem-4-carboxylic acid,
7β-[2-(2-aminothiazol-4-yl)-(Z)-2-methoxyiminoacetamido]-3-[[1-(3-guanidinopropyl)-1H-tetrazol-5-yl]thiometyl]-3-cephem-4-carboxylic acid or
3-[(3-amidinomethylthio-4-cyanoisothiazol-5-yl)thiomethyl]-7β-[2-(2-aminothiazol-4-yl)-(Z)-2-methoxyiminoacetamido]-3-cephem- 4-carboxylic acid or pharmacologically acceptable salt thereof.

14. An antibacterial composition which comprises an effective anti-bacterial amount of a compound claimed in claim 1 or a pharmacologically acceptable salt thereof and a pharmaceutically acceptable carrier or excipient.

* * * * *